US006868875B2

(12) United States Patent  
De Beukeleer et al.

(10) Patent No.: US 6,868,875 B2
(45) Date of Patent: Mar. 22, 2005

(54) METHOD AND APPARATUS FOR DISPENSING A LIQUID INTO A SERIES OF WELLS

(75) Inventors: Werner René Irène De Beukeleer, Vremde (BE); Christiaan Hubert Simon Roelant, Leuven (BE)

(73) Assignee: Tibotec BVBA, Mechelen (BE)

( * ) Notice: Subject to any disclaimer, the term of this patent is extended or adjusted under 35 U.S.C. 154(b) by 0 days.

(21) Appl. No.: 10/220,931
(22) PCT Filed: Mar. 8, 2001
(86) PCT No.: PCT/EP01/02808
§ 371 (c)(1),
(2), (4) Date: Feb. 5, 2003
(87) PCT Pub. No.: WO01/67114
PCT Pub. Date: Sep. 13, 2001

(65) Prior Publication Data
US 2003/0155034 A1 Aug. 21, 2003

(30) Foreign Application Priority Data
Mar. 8, 2000 (EP) .............................................. 00200813

(51) Int. Cl.⁷ ................................................. B65B 1/04
(52) U.S. Cl. ......................... 141/130; 422/99; 422/100
(58) Field of Search ............................... 141/130, 250, 141/267, 270; 422/99, 100, 116, 131, 110, 111, 130

(56) References Cited

U.S. PATENT DOCUMENTS 6,001,311 A  *  12/1999  Brennan ..................... 422/131
6,063,339 A       5/2000  Tisone et al.

FOREIGN PATENT DOCUMENTS

| DE | 84 38 264 U1 |   | 7/1985 |
| EP | 0 037 502 | * | 8/1999 |
| EP | 0937502 B1 |   | 8/1999 |
| FR | 2 609 808 A1 | * | 1/1987 |
| FR | 2609808 A1 |   | 7/1988 |
| WO | WO 97/42832 A1 |   | 11/1997 |
| WO | WO 99/34931 A1 |   | 7/1999 |
| WO | WO 99/34931 | * | 7/1999 |

* cited by examiner

Primary Examiner—Steven O. Douglas
(74) Attorney, Agent, or Firm—Woodcock Washburn LLP

(57) ABSTRACT

A method for dispensing a volume of fluids from a reservoir, through a fluid outlet in fluid communication with said reservoir, into each well of at least a series of wells, whereby the fluid is dispensed into said series of wells at a continuous uninterrupted flow. A micro titer plate constructed from a hydrophobic and more in particular from a plastic material containing a plurality of series of wells and to an apparatus able to perform the above method.

19 Claims, 12 Drawing Sheets

Average deviation over plate 1: 4%
Percentage deviation per well - plate 1:

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|----|----|----|----|----|----|----|----|----|----|----|----|----|----|----|
| A | 18% | 1% | 0% | 1% | 1% | 1% | 1% | 1% | 3% | 2% | 3% | 2% | 2% | 1% | 2% | 2% | 3% | 3% | 5% | 5% | 6% | 8% | 9% | 11% |
| B | 6% | 3% | 2% | 2% | 1% | 1% | 0% | 0% | 0% | 1% | 2% | 2% | 2% | 1% | 2% | 1% | 1% | 1% | 1% | 3% | 2% | 3% | 3% | 3% |
| C | 0% | 1% | 3% | 2% | 3% | 3% | 1% | 1% | 0% | 1% | 1% | 0% | 0% | 2% | 0% | 1% | 0% | 0% | 1% | 0% | 0% | 2% | 1% | 0% |
| D | 2% | 2% | 1% | 1% | 1% | 1% | 0% | 2% | 1% | 2% | 2% | 1% | 1% | 1% | 1% | 1% | 1% | 2% | 1% | 2% | 1% | 0% | 0% | 1% |
| E | 0% | 0% | 1% | 0% | 0% | 1% | 1% | 1% | 2% | 1% | 2% | 3% | 1% | 2% | 2% | 3% | 2% | 1% | 1% | 3% | 3% | 3% | 1% | 2% |
| F | 18% | 1% | 1% | 1% | 1% | 1% | 0% | 1% | 1% | 2% | 2% | 1% | 1% | 2% | 2% | 2% | 2% | 1% | 2% | 2% | 2% | 1% | 0% | 0% |
| G | 1% | 1% | 2% | 3% | 1% | 0% | 1% | 1% | 1% | 1% | 0% | 1% | 0% | 1% | 1% | 0% | 0% | 0% | 2% | 1% | 0% | 1% | 0% | 0% |
| H | 1% | 2% | 3% | 2% | 0% | 1% | 1% | 1% | 2% | 1% | 0% | 1% | 0% | 1% | 2% | 0% | 1% | 0% | 0% | 1% | 1% | 1% | 1% | 2% |
| I | 21% | 1% | 2% | 1% | 0% | 1% | 0% | 1% | 1% | 0% | 0% | 1% | 0% | 0% | 0% | 2% | 1% | 1% | 0% | 0% | 0% | 0% | 0% | 1% |
| J | 3% | 0% | 1% | 1% | 0% | 0% | 0% | 1% | 0% | 1% | 0% | 1% | 1% | 0% | 1% | 1% | 1% | 0% | 0% | 0% | 0% | 1% | 1% | 2% |
| K | 5% | 0% | 0% | 0% | 0% | 0% | 0% | 1% | 0% | 0% | 1% | 1% | 0% | 1% | 2% | 2% | 2% | 2% | 0% | 0% | 1% | 0% | 1% | 0% |
| L | 1% | 1% | 1% | 1% | 2% | 0% | 0% | 0% | 1% | 0% | 1% | 2% | 0% | 1% | 1% | 3% | 2% | 1% | 2% | 0% | 2% | 2% | 0% | 0% |
| M | 0% | 0% | 1% | 2% | 2% | 1% | 1% | 2% | 2% | 1% | 1% | 0% | 2% | 0% | 0% | 1% | 1% | 1% | 0% | 0% | 2% | 0% | 2% | 1% |
| N | 16% | 0% | 2% | 2% | 2% | 2% | 1% | 1% | 1% | 1% | 2% | 1% | 1% | 1% | 1% | 1% | 1% | 1% | 1% | 1% | 0% | 2% | 0% | 1% | 1% |
| O | 4% | 3% | 3% | 2% | 1% | 1% | 2% | 1% | 1% | 2% | 2% | 1% | 3% | 1% | 2% | 1% | 1% | 1% | 1% | 0% | 2% | 1% | 1% | 1% |
| P | 2% | 6% | 5% | 4% | 2% | 1% | 1% | 1% | 0% | 1% | 2% | 1% | 3% | 1% | 1% | 1% | 1% | 2% | 2% | 2% | 2% | 4% | 2% | 1% |
| Q | 22% | 5% | 4% | 2% | 0% | 6% | 3% | 1% | 3% | 1% | 3% | 2% | 2% | 0% | 1% | 2% | 0% | 2% | 2% | 2% | 2% | 1% | 1% | 1% |
| R | 24% | 5% | 4% | 2% | 1% | 3% | 4% | 0% | 2% | 2% | 4% | 2% | 2% | 2% | 2% | 3% | 3% | 2% | 1% | 1% | 1% | 0% | 1% | 0% |
| S | 14% | 10% | 0% | 0% | 0% | 1% | 4% | 0% | 2% | 1% | 2% | 1% | 0% | 1% | 1% | 1% | 1% | 1% | 0% | 1% | 1% | 0% | 1% | 0% |
| T | 10% | 8% | 0% | 0% | 1% | 0% | 2% | 1% | 2% | 0% | 0% | 1% | 0% | 0% | 1% | 1% | 1% | 2% | 1% | 0% | 1% | 0% | 3% | 2% |
| U | 18% | 9% | 2% | 3% | 2% | 1% | 1% | 2% | 0% | 0% | 0% | 0% | 1% | 0% | 1% | 1% | 1% | 1% | 1% | 0% | 2% | 2% | 3% | 0% |
| V | 11% | 12% | 2% | 0% | 3% | 0% | 1% | 2% | 1% | 0% | 0% | 0% | 0% | 0% | 1% | 2% | 0% | 2% | 2% | 2% | 0% | 1% | 5% | 1% |
| W | 14% | 12% | 3% | 0% | 4% | 0% | 2% | 3% | 0% | 1% | 0% | 1% | 1% | 1% | 2% | 2% | 1% | 0% | 1% | 1% | 1% | 0% | 4% | 2% |
| X | 12% | 12% | 1% | 1% | 4% | 2% | 1% | 3% | 0% | 0% | 1% | 1% | 1% | 3% | 1% | 1% | 1% | 1% | 1% | 1% | 1% | 2% | 3% | 1% |
| Y | 23% | 11% | 2% | 3% | 5% | 3% | 0% | 4% | 0% | 2% | 2% | 0% | 0% | 2% | 1% | 0% | 0% | 0% | 0% | 0% | 0% | 0% | 3% | 1% |
| Z | 25% | 7% | 4% | 3% | 2% | 3% | 2% | 4% | 2% | 2% | 0% | 1% | 1% | 1% | 1% | 0% | 1% | 0% | 1% | 1% | 0% | 0% | 3% | 0% |
| AA | 30% | 9% | 3% | 3% | 4% | 3% | 3% | 5% | 2% | 3% | 2% | 1% | 3% | 0% | 2% | 2% | 2% | 1% | 1% | 1% | 1% | 1% | 2% | 1% |
| AB | 3% | 13% | 4% | 1% | 4% | 2% | 1% | 4% | 2% | 3% | 3% | 1% | 2% | 0% | 2% | 1% | 2% | 1% | 0% | 2% | 2% | 0% | 1% | 0% |
| AC | 25% | 11% | 1% | 2% | 3% | 0% | 0% | 4% | 0% | 2% | 2% | 0% | 1% | 2% | 1% | 1% | 1% | 0% | 1% | 0% | 1% | 1% | 3% | 1% |
| AD | 30% | 9% | 1% | 1% | 2% | 0% | 0% | 1% | 3% | 1% | 1% | 2% | 2% | 3% | 1% | 4% | 1% | 2% | 2% | 1% | 3% | 0% | 3% | 3% |
| AE | 22% | 9% | 1% | 2% | 2% | 1% | 1% | 2% | 3% | 1% | 2% | 1% | 3% | 4% | 2% | 5% | 1% | 3% | 3% | 2% | 3% | 3% | 4% | 3% |
| AF | 21% | 10% | 1% | 1% | 1% | 0% | 2% | 2% | 5% | 0% | 1% | 3% | 1% | 2% | 2% | 4% | 5% | 6% | 7% | 8% | 9% | 8% | 11% | 13% |

Figure 6

Average deviation over plate 1: 4%
Percentage deviation per well - plate 1:

|    | 25  | 26  | 27 | 28  | 29 | 30 | 31 | 32 | 33 | 34 | 35 | 36 | 37 | 38 | 39 | 40 | 41 | 42 | 43 | 44 | 45 | 46 | 47  | 48  |
|----|-----|-----|----|-----|----|----|----|----|----|----|----|----|----|----|----|----|----|----|----|----|----|----|-----|-----|
| A  | 11% | 9%  | 7% | 7%  | 6% | 5% | 5% | 5% | 3% | 3% | 3% | 3% | 3% | 3% | 4% | 4% | 3% | 1% | 1% | 2% | 2% | 4% | 7%  | 20% |
| B  | 2%  | 4%  | 3% | 2%  | 3% | 1% | 3% | 1% | 2% | 2% | 2% | 3% | 4% | 2% | 2% | 2% | 1% | 1% | 1% | 0% | 2% | 2% | 9%  | 31% |
| C  | 0%  | 2%  | 1% | 0%  | 2% | 0% | 2% | 0% | 2% | 2% | 0% | 1% | 1% | 1% | 1% | 1% | 0% | 1% | 2% | 0% | 3% | 4% | 10% | 29% |
| D  | 2%  | 0%  | 0% | 1%  | 0% | 0% | 1% | 1% | 1% | 1% | 1% | 0% | 0% | 0% | 0% | 1% | 0% | 1% | 2% | 2% | 3% | 3% | 13% | 18% |
| E  | 2%  | 1%  | 2% | 2%  | 0% | 2% | 1% | 3% | 1% | 1% | 2% | 2% | 1% | 2% | 0% | 0% | 1% | 2% | 0% | 2% | 5% | 6% | 10% | 24% |
| F  | 2%  | 1%  | 1% | 3%  | 1% | 2% | 0% | 1% | 1% | 0% | 1% | 2% | 1% | 1% | 1% | 2% | 2% | 1% | 1% | 2% | 3% | 2% | 12% | 19% |
| G  | 0%  | 0%  | 0% | 1%  | 0% | 1% | 0% | 1% | 0% | 1% | 0% | 1% | 0% | 1% | 2% | 1% | 2% | 2% | 0% | 2% | 2% | 2% | 13% | 19% |
| H  | 3%  | 1%  | 1% | 0%  | 1% | 1% | 1% | 2% | 2% | 2% | 2% | 1% | 0% | 1% | 1% | 0% | 1% | 1% | 0% | 1% | 2% | 0% | 12% | 21% |
| I  | 1%  | 1%  | 1% | 1%  | 1% | 0% | 1% | 0% | 1% | 2% | 2% | 1% | 1% | 1% | 0% | 2% | 1% | 1% | 0% | 3% | 2% | 1% | 13% | 20% |
| J  | 2%  | 3%  | 1% | 0%  | 2% | 0% | 1% | 1% | 1% | 0% | 1% | 1% | 1% | 0% | 0% | 1% | 1% | 0% | 0% | 2% | 3% | 2% | 11% | 21% |
| K  | 0%  | 2%  | 0% | 1%  | 1% | 0% | 1% | 1% | 1% | 1% | 1% | 1% | 1% | 0% | 0% | 0% | 0% | 0% | 2% | 1% | 3% | 2% | 13% | 28% |
| L  | 1%  | 0%  | 1% | 1%  | 1% | 1% | 0% | 1% | 1% | 1% | 0% | 0% | 0% | 1% | 1% | 1% | 1% | 1% | 1% | 3% | 0% | 2% | 14% | 1%  |
| M  | 0%  | 0%  | 1% | 1%  | 1% | 1% | 2% | 1% | 1% | 1% | 0% | 1% | 1% | 2% | 1% | 1% | 1% | 1% | 2% | 1% | 2% | 1% | 11% | 30% |
| N  | 0%  | 1%  | 1% | 2%  | 1% | 1% | 1% | 1% | 1% | 3% | 2% | 1% | 1% | 2% | 2% | 0% | 2% | 0% | 1% | 1% | 0% | 1% | 14% | 18% |
| O  | 1%  | 2%  | 0% | 1%  | 1% | 1% | 1% | 2% | 1% | 3% | 3% | 3% | 1% | 3% | 2% | 2% | 1% | 1% | 3% | 0% | 1% | 1% | 11% | 26% |
| P  | 0%  | 1%  | 4% | 2%  | 3% | 1% | 1% | 2% | 1% | 2% | 0% | 0% | 0% | 1% | 1% | 0% | 1% | 1% | 2% | 1% | 1% | 3% | 7%  | 22% |
| Q  | 1%  | 0%  | 3% | 2%  | 1% | 3% | 1% | 2% | 1% | 3% | 4% | 0% | 2% | 0% | 3% | 1% | 3% | 1% | 3% | 3% | 1% | 3% | 1%  | 2%  |
| R  | 0%  | 0%  | 1% | 0%  | 1% | 3% | 1% | 3% | 1% | 3% | 3% | 1% | 3% | 2% | 3% | 1% | 3% | 1% | 3% | 3% | 1% | 3% | 1%  | 6%  |
| S  | 1%  | 1%  | 0% | 1%  | 0% | 2% | 0% | 1% | 1% | 1% | 2% | 1% | 2% | 1% | 2% | 0% | 2% | 0% | 1% | 3% | 1% | 2% | 1%  | 18% |
| T  | 0%  | 2%  | 2% | 0%  | 1% | 1% | 1% | 2% | 0% | 2% | 1% | 1% | 2% | 0% | 2% | 0% | 1% | 0% | 1% | 2% | 0% | 1% | 1%  | 0%  |
| U  | 1%  | 2%  | 0% | 0%  | 1% | 3% | 1% | 2% | 1% | 1% | 1% | 2% | 0% | 0% | 1% | 0% | 2% | 0% | 1% | 2% | 1% | 2% | 2%  | 1%  |
| V  | 3%  | 3%  | 1% | 2%  | 2% | 2% | 1% | 0% | 1% | 0% | 2% | 0% | 0% | 1% | 1% | 0% | 3% | 1% | 3% | 2% | 0% | 2% | 2%  | 11% |
| W  | 2%  | 2%  | 2% | 2%  | 1% | 1% | 1% | 3% | 1% | 2% | 1% | 0% | 0% | 1% | 1% | 1% | 2% | 1% | 2% | 0% | 0% | 0% | 1%  | 2%  |
| X  | 3%  | 2%  | 2% | 1%  | 1% | 3% | 1% | 2% | 1% | 3% | 4% | 1% | 1% | 1% | 0% | 1% | 2% | 2% | 1% | 1% | 1% | 1% | 0%  |     |
| Y  | 2%  | 2%  | 1% | 1%  | 1% | 2% | 1% | 1% | 2% | 2% | 3% | 1% | 1% | 0% | 0% | 1% | 1% | 0% | 1% | 1% | 1% | 1% | 1%  | 2%  |
| Z  | 1%  | 1%  | 0% | 1%  | 0% | 1% | 0% | 1% | 0% | 2% | 1% | 1% | 1% | 0% | 0% | 1% | 1% | 0% | 1% | 1% | 1% | 2% | 2%  |     |
| AA | 1%  | 1%  | 0% | 1%  | 1% | 1% | 0% | 1% | 1% | 0% | 1% | 1% | 1% | 0% | 0% | 1% | 1% | 3% | 1% | 0% | 2% | 0% | 2%  | 0%  |
| AB | 1%  | 1%  | 1% | 2%  | 1% | 1% | 0% | 2% | 0% | 1% | 0% | 0% | 1% | 1% | 1% | 2% | 2% | 1% | 1% | 1% | 2% | 1% | 3%  | 1%  |
| AC | 0%  | 2%  | 3% | 3%  | 1% | 2% | 1% | 2% | 2% | 0% | 1% | 2% | 2% | 0% | 1% | 1% | 1% | 0% | 0% | 0% | 2% | 0% | 2%  | 2%  |
| AD | 3%  | 3%  | 3% | 5%  | 3% | 4% | 2% | 4% | 3% | 3% | 5% | 4% | 4% | 2% | 3% | 1% | 1% | 0% | 1% | 1% | 0% | 0% | 2%  | 2%  |
| AE | 4%  | 5%  | 4% | 5%  | 3% | 5% | 3% | 4% | 4% | 3% | 5% | 5% | 5% | 6% | 4% | 5% | 5% | 2% | 1% | 0% | 1% | 0% | 2%  | 1%  |
| AF | 14% | 12% | 9% | 10% | 8% | 9% | 6% | 6% | 4% | 4% | 4% | 3% | 4% | 3% | 5% | 4% | 4% | 3% | 3% | 4% | 1% | 2% | 2%  | 2%  |

Figure 6 (Cont.)

Average deviation over plate 2: 5%
Percentage deviation per well - plate 2:

|    | 1   | 2   | 3  | 4  | 5  | 6  | 7  | 8  | 9  | 10 | 11 | 12 | 13 | 14 | 15 | 16 | 17 | 18 | 19  | 20  | 21  | 22  | 23  | 24  |
|----|-----|-----|----|----|----|----|----|----|----|----|----|----|----|----|----|----|----|----|-----|-----|-----|-----|-----|-----|
| A  | 8%  | 3%  | 4% | 4% | 5% | 4% | 4% | 5% | 7% | 7% | 7% | 8% | 7% | 6% | 8% | 8% | 7% | 8% | 10% | 10% | 10% | 12% | 13% | 17% |
| B  | 7%  | 2%  | 1% | 2% | 1% | 0% | 1% | 0% | 0% | 1% | 2% | 3% | 2% | 3% | 3% | 2% | 2% | 2% | 1%  | 3%  | 4%  | 4%  | 4%  | 3%  |
| C  | 1%  | 1%  | 1% | 0% | 2% | 3% | 1% | 2% | 2% | 2% | 1% | 0% | 0% | 0% | 0% | 1% | 1% | 1% | 0%  | 1%  | 0%  | 2%  | 2%  | 2%  |
| D  | 0%  | 0%  | 0% | 1% | 1% | 3% | 0% | 2% | 2% | 2% | 2% | 3% | 3% | 2% | 1% | 1% | 2% | 2% | 2%  | 1%  | 1%  | 0%  | 1%  | 3%  |
| E  | 2%  | 1%  | 0% | 1% | 1% | 0% | 2% | 2% | 2% | 2% | 3% | 3% | 2% | 3% | 3% | 4% | 3% | 2% | 3%  | 3%  | 2%  | 1%  | 1%  | 2%  |
| F  | 25% | 2%  | 0% | 0% | 0% | 1% | 1% | 3% | 2% | 2% | 2% | 1% | 2% | 2% | 3% | 3% | 2% | 1% | 2%  | 2%  | 2%  | 1%  | 0%  | 1%  |
| G  | 2%  | 1%  | 0% | 1% | 0% | 1% | 2% | 2% | 2% | 2% | 1% | 2% | 1% | 1% | 0% | 1% | 0% | 1% | 2%  | 1%  | 1%  | 0%  | 2%  | 2%  |
| H  | 12% | 1%  | 1% | 1% | 1% | 0% | 1% | 1% | 2% | 0% | 0% | 1% | 0% | 0% | 0% | 0% | 0% | 1% | 1%  | 0%  | 0%  | 1%  | 1%  | 2%  |
| I  | 21% | 1%  | 1% | 1% | 0% | 1% | 1% | 1% | 1% | 1% | 1% | 2% | 1% | 2% | 1% | 1% | 1% | 0% | 1%  | 1%  | 0%  | 1%  | 1%  | 2%  |
| J  | 2%  | 0%  | 0% | 0% | 0% | 0% | 0% | 1% | 1% | 1% | 1% | 1% | 1% | 1% | 3% | 1% | 2% | 1% | 1%  | 0%  | 1%  | 1%  | 0%  | 1%  | 2% |
| K  | 8%  | 0%  | 1% | 1% | 1% | 2% | 0% | 1% | 1% | 1% | 1% | 2% | 1% | 2% | 3% | 2% | 2% | 2% | 0%  | 0%  | 2%  | 2%  | 1%  | 0%  |
| L  | 3%  | 1%  | 1% | 1% | 0% | 0% | 1% | 0% | 1% | 1% | 0% | 1% | 0% | 2% | 3% | 3% | 2% | 1% | 1%  | 2%  | 2%  | 1%  | 1%  | 0%  |
| M  | 5%  | 1%  | 1% | 1% | 0% | 2% | 1% | 1% | 0% | 2% | 1% | 1% | 0% | 2% | 3% | 1% | 0% | 0% | 1%  | 1%  | 2%  | 2%  | 1%  | 2%  |
| N  | 23% | 1%  | 1% | 0% | 1% | 1% | 1% | 1% | 1% | 0% | 0% | 0% | 0% | 1% | 1% | 0% | 0% | 0% | 1%  | 1%  | 2%  | 1%  | 2%  | 2%  |
| O  | 6%  | 0%  | 1% | 1% | 0% | 1% | 1% | 1% | 2% | 0% | 0% | 1% | 0% | 0% | 1% | 1% | 1% | 0% | 0%  | 1%  | 2%  | 1%  | 3%  | 2%  |
| P  | 1%  | 3%  | 4% | 3% | 1% | 0% | 1% | 2% | 2% | 0% | 1% | 1% | 0% | 1% | 0% | 2% | 0% | 0% | 0%  | 0%  | 1%  | 2%  | 0%  | 2%  |
| Q  | 23% | 3%  | 6% | 5% | 3% | 7% | 4% | 3% | 6% | 2% | 4% | 3% | 4% | 3% | 3% | 4% | 2% | 3% | 4%  | 3%  | 4%  | 1%  | 2%  | 1%  |
| R  | 25% | 6%  | 4% | 2% | 2% | 4% | 3% | 0% | 3% | 1% | 1% | 2% | 2% | 3% | 1% | 2% | 2% | 2% | 1%  | 0%  | 1%  | 0%  | 3%  | 1%  |
| S  | 14% | 11% | 1% | 1% | 0% | 1% | 1% | 1% | 2% | 0% | 0% | 0% | 0% | 1% | 1% | 1% | 1% | 1% | 1%  | 0%  | 0%  | 0%  | 1%  | 1%  |
| T  | 9%  | 1%  | 2% | 1% | 1% | 0% | 1% | 2% | 1% | 1% | 0% | 0% | 0% | 0% | 2% | 1% | 1% | 2% | 1%  | 1%  | 0%  | 0%  | 2%  | 3%  |
| U  | 11% | 11% | 3% | 2% | 3% | 1% | 0% | 3% | 1% | 1% | 2% | 0% | 1% | 1% | 2% | 1% | 1% | 1% | 2%  | 1%  | 0%  | 2%  | 3%  | 0%  |
| V  | 17% | 13% | 2% | 2% | 2% | 1% | 0% | 3% | 1% | 1% | 1% | 2% | 1% | 3% | 3% | 1% | 0% | 0% | 1%  | 1%  | 0%  | 1%  | 3%  | 1%  |
| W  | 14% | 15% | 3% | 2% | 3% | 1% | 0% | 4% | 1% | 2% | 1% | 1% | 1% | 1% | 1% | 1% | 2% | 0% | 1%  | 1%  | 1%  | 1%  | 4%  | 3%  |
| X  | 29% | 11% | 1% | 2% | 2% | 1% | 0% | 3% | 1% | 2% | 2% | 0% | 0% | 2% | 1% | 0% | 1% | 1% | 2%  | 1%  | 1%  | 1%  | 3%  | 2%  |
| Y  | 24% | 12% | 4% | 3% | 5% | 3% | 1% | 4% | 2% | 2% | 3% | 1% | 0% | 2% | 1% | 2% | 1% | 1% | 1%  | 0%  | 1%  | 1%  | 4%  | 0%  |
| Z  | 35% | 9%  | 2% | 3% | 3% | 3% | 2% | 4% | 2% | 1% | 2% | 1% | 2% | 2% | 1% | 0% | 0% | 1% | 1%  | 2%  | 0%  | 1%  | 2%  | 1%  |
| AA | 29% | 12% | 4% | 3% | 4% | 3% | 3% | 5% | 3% | 3% | 2% | 1% | 2% | 1% | 2% | 2% | 2% | 1% | 1%  | 2%  | 0%  | 1%  | 1%  | 1%  |
| AB | 28% | 12% | 4% | 3% | 4% | 2% | 2% | 5% | 2% | 3% | 3% | 1% | 3% | 2% | 2% | 1% | 2% | 2% | 1%  | 1%  | 0%  | 1%  | 1%  | 2%  |
| AC | 25% | 12% | 4% | 4% | 4% | 3% | 2% | 5% | 1% | 4% | 3% | 1% | 2% | 1% | 1% | 1% | 1% | 2% | 0%  | 2%  | 0%  | 1%  | 2%  | 0%  |
| AD | 38% | 10% | 3% | 3% | 3% | 1% | 3% | 3% | 1% | 2% | 1% | 2% | 1% | 3% | 2% | 1% | 1% | 1% | 0%  | 1%  | 2%  | 1%  | 2%  | 0%  |
| AE | 32% | 10% | 2% | 4% | 4% | 3% | 2% | 1% | 1% | 0% | 1% | 3% | 2% | 3% | 0% | 2% | 0% | 1% | 1%  | 1%  | 2%  | 2%  | 3%  | 1%  |
| AF | 22% | 13% | 3% | 3% | 3% | 1% | 1% | 1% | 3% | 1% | 1% | 1% | 1% | 2% | 0% | 2% | 4% | 4% | 5%  | 5%  | 8%  | 7%  | 9%  | 10% |

Figure 7

Average deviation over plate 2: 5%
Percentage deviation per well - plate 2:

| | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|---|---|---|---|---|---|---|---|---|
| A | 16% | 12% | 12% | 12% | 12% | 13% | 11% | 9% | 10% | 9% | 10% | 10% | 9% | 9% | 8% | 9% | 9% | 6% | 7% | 7% | 4% | 5% | 2% | 23% |
| B | 3% | 4% | 4% | 4% | 3% | 2% | 5% | 3% | 3% | 4% | 4% | 5% | 5% | 4% | 4% | 2% | 3% | 2% | 3% | 1% | 0% | 2% | 8% | 12% |
| C | 2% | 2% | 3% | 0% | 2% | 1% | 2% | 2% | 2% | 2% | 1% | 2% | 1% | 1% | 1% | 1% | 1% | 1% | 3% | 0% | 2% | 2% | 9% | 29% |
| D | 1% | 1% | 0% | 1% | 0% | 0% | 1% | 0% | 0% | 1% | 1% | 0% | 1% | 1% | 0% | 1% | 1% | 0% | 2% | 1% | 2% | 0% | 10% | 21% |
| E | 2% | 0% | 0% | 2% | 0% | 2% | 1% | 3% | 2% | 0% | 2% | 1% | 2% | 1% | 0% | 1% | 0% | 0% | 0% | 3% | 2% | 3% | 12% | 13% |
| F | 3% | 1% | 1% | 1% | 1% | 2% | 1% | 2% | 1% | 1% | 1% | 0% | 1% | 1% | 2% | 1% | 1% | 0% | 1% | 2% | 2% | 1% | 11% | 22% |
| G | 2% | 1% | 1% | 0% | 0% | 1% | 1% | 1% | 0% | 1% | 0% | 1% | 0% | 0% | 1% | 1% | 2% | 1% | 1% | 2% | 2% | 1% | 12% | 19% |
| H | 0% | 1% | 1% | 0% | 1% | 1% | 2% | 2% | 2% | 3% | 1% | 1% | 1% | 0% | 1% | 0% | 1% | 1% | 1% | 2% | 1% | 0% | 13% | 15% |
| I | 0% | 1% | 1% | 0% | 0% | 0% | 1% | 1% | 1% | 2% | 1% | 1% | 1% | 1% | 0% | 1% | 1% | 1% | 0% | 1% | 0% | 0% | 14% | 17% |
| J | 1% | 1% | 2% | 1% | 1% | 1% | 2% | 0% | 1% | 1% | 1% | 2% | 0% | 1% | 1% | 1% | 2% | 1% | 1% | 2% | 3% | 1% | 11% | 26% |
| K | 0% | 1% | 1% | 1% | 1% | 1% | 1% | 1% | 1% | 1% | 2% | 1% | 1% | 0% | 1% | 1% | 0% | 0% | 0% | 2% | 1% | 1% | 14% | 25% |
| L | 0% | 1% | 0% | 2% | 0% | 1% | 0% | 1% | 1% | 0% | 1% | 1% | 0% | 1% | 1% | 0% | 1% | 0% | 0% | 2% | 2% | 3% | 14% | 2% |
| M | 1% | 1% | 0% | 2% | 0% | 0% | 2% | 1% | 0% | 1% | 0% | 1% | 0% | 2% | 2% | 0% | 1% | 0% | 1% | 2% | 1% | 0% | 14% | 24% |
| N | 1% | 1% | 1% | 3% | 1% | 0% | 1% | 0% | 1% | 2% | 1% | 1% | 1% | 2% | 1% | 2% | 1% | 0% | 2% | 0% | 0% | 0% | 15% | 21% |
| O | 2% | 1% | 0% | 1% | 2% | 2% | 2% | 1% | 0% | 2% | 2% | 4% | 1% | 2% | 2% | 1% | 1% | 1% | 2% | 1% | 1% | 0% | 9% | 22% |
| P | 1% | 1% | 2% | 2% | 3% | 2% | 2% | 0% | 0% | 0% | 0% | 1% | 1% | 0% | 0% | 1% | 1% | 1% | 2% | 0% | 2% | 1% | 10% | 0% |
| Q | 1% | 1% | 3% | 7% | 4% | 7% | 3% | 6% | 4% | 6% | 6% | 4% | 6% | 4% | 5% | 4% | 4% | 3% | 5% | 4% | 3% | 3% | 2% | 3% |
| R | 0% | 1% | 1% | 2% | 2% | 4% | 4% | 4% | 2% | 4% | 5% | 3% | 5% | 2% | 5% | 2% | 5% | 2% | 4% | 3% | 3% | 3% | 2% | 0% |
| S | 2% | 3% | 0% | 0% | 0% | 3% | 1% | 3% | 0% | 4% | 3% | 2% | 3% | 0% | 4% | 0% | 3% | 1% | 3% | 3% | 2% | 3% | 0% | 22% |
| T | 0% | 2% | 1% | 2% | 1% | 3% | 1% | 3% | 1% | 4% | 2% | 1% | 3% | 0% | 3% | 0% | 3% | 0% | 1% | 2% | 0% | 2% | 0% | 1% |
| U | 2% | 2% | 1% | 2% | 3% | 4% | 1% | 2% | 1% | 2% | 2% | 0% | 1% | 1% | 7% | 0% | 2% | 2% | 3% | 3% | 1% | 2% | 0% | 1% |
| V | 1% | 4% | 2% | 3% | 2% | 4% | 2% | 1% | 0% | 1% | 2% | 0% | 1% | 0% | 2% | 1% | 3% | 2% | 3% | 3% | 0% | 2% | 0% | 11% |
| W | 2% | 2% | 3% | 2% | 2% | 3% | 1% | 4% | 0% | 2% | 2% | 1% | 2% | 1% | 3% | 0% | 3% | 1% | 2% | 2% | 0% | 2% | 0% | 2% |
| X | 3% | 1% | 3% | 2% | 2% | 2% | 0% | 2% | 1% | 3% | 4% | 2% | 3% | 1% | 2% | 0% | 3% | 2% | 2% | 3% | 1% | 1% | 0% | 2% |
| Y | 1% | 1% | 2% | 1% | 2% | 2% | 0% | 2% | 2% | 3% | 3% | 2% | 3% | 1% | 2% | 0% | 2% | 0% | 1% | 2% | 0% | 1% | 1% | 4% |
| Z | 1% | 1% | 2% | 3% | 1% | 1% | 0% | 1% | 0% | 1% | 2% | 1% | 3% | 1% | 2% | 1% | 2% | 1% | 1% | 2% | 0% | 1% | 1% | 1% |
| AA | 1% | 1% | 0% | 1% | 1% | 2% | 0% | 0% | 1% | 0% | 0% | 1% | 1% | 1% | 0% | 2% | 0% | 2% | 0% | 2% | 1% | 0% | 2% | 1% |
| AB | 0% | 1% | 1% | 2% | 1% | 3% | 0% | 2% | 1% | 1% | 0% | 0% | 0% | 2% | 1% | 3% | 1% | 1% | 2% | 3% | 2% | 1% | 2% | 2% |
| AC | 0% | 1% | 2% | 1% | 1% | 3% | 2% | 2% | 2% | 2% | 0% | 1% | 1% | 2% | 0% | 2% | 2% | 0% | 2% | 0% | 2% | 1% | 2% | 3% |
| AD | 0% | 2% | 3% | 2% | 2% | 3% | 2% | 2% | 3% | 2% | 1% | 1% | 2% | 0% | 2% | 0% | 1% | 1% | 0% | 2% | 0% | 1% | 2% | 1% |
| AE | 2% | 3% | 3% | 3% | 3% | 3% | 2% | 2% | 3% | 2% | 3% | 2% | 3% | 1% | 3% | 2% | 2% | 0% | 0% | 1% | 2% | 1% | 2% | 1% |
| AF | 13% | 9% | 8% | 9% | 7% | 7% | 4% | 4% | 3% | 3% | 2% | 2% | 3% | 1% | 5% | 3% | 4% | 2% | 2% | 2% | 0% | 2% | 2% | 2% |

Figure 7 (Cont.)

Average deviation over plate 1: 3%
Percentage deviation per well - plate 1:

|    | 1  | 2  | 3  | 4  | 5  | 6  | 7  | 8  | 9  | 10 | 11 | 12 | 13 | 14 | 15 | 16 | 17 | 18 | 19 | 20 | 21 | 22 | 23 | 24  |
|----|----|----|----|----|----|----|----|----|----|----|----|----|----|----|----|----|----|----|----|----|----|----|----|-----|
| A  | 4% | 2% | 5% | 0% | 4% | 0% | 4% | 2% | 0% | 1% | 1% | 5% | 2% | 2% | 1% | 4% | 1% | 3% | 2% | 6% | 1% | 7% | 5% | 11% |
| B  | 3% | 1% | 2% | 1% | 5% | 1% | 3% | 1% | 2% | 1% | 1% | 5% | 2% | 3% | 0% | 4% | 1% | 2% | 0% | 4% | 1% | 3% | 0% | 3%  |
| C  | 5% | 0% | 3% | 1% | 1% | 2% | 3% | 1% | 2% | 0% | 3% | 3% | 2% | 2% | 1% | 3% | 1% | 1% | 2% | 2% | 2% | 2% | 2% | 1%  |
| D  | 5% | 1% | 3% | 1% | 2% | 1% | 3% | 0% | 3% | 0% | 3% | 2% | 3% | 6% | 3% | 1% | 3% | 0% | 4% | 1% | 4% | 0% | 2% | 0%  |
| E  | 8% | 0% | 4% | 1% | 6% | 1% | 5% | 1% | 5% | 1% | 5% | 1% | 6% | 1% | 4% | 0% | 6% | 2% | 5% | 0% | 5% | 2% | 3% | 0%  |
| F  | 8% | 0% | 4% | 1% | 4% | 0% | 4% | 1% | 5% | 1% | 4% | 1% | 5% | 0% | 2% | 1% | 4% | 0% | 3% | 1% | 4% | 0% | 3% | 0%  |
| G  | 7% | 0% | 4% | 0% | 4% | 0% | 4% | 1% | 5% | 0% | 4% | 1% | 2% | 2% | 0% | 2% | 2% | 1% | 4% | 1% | 3% | 1% | 2% | 2%  |
| H  | 6% | 1% | 3% | 2% | 4% | 1% | 3% | 1% | 3% | 1% | 3% | 0% | 1% | 4% | 3% | 4% | 1% | 3% | 2% | 1% | 3% | 1% | 2% | 3%  |
| I  | 6% | 0% | 4% | 1% | 4% | 2% | 4% | 1% | 3% | 1% | 3% | 1% | 3% | 2% | 2% | 1% | 2% | 2% | 2% | 1% | 3% | 0% | 2% | 2%  |
| J  | 7% | 1% | 3% | 1% | 4% | 0% | 2% | 1% | 4% | 1% | 2% | 1% | 4% | 0% | 3% | 1% | 3% | 2% | 1% | 2% | 2% | 1% | 1% | 3%  |
| K  | 7% | 0% | 4% | 0% | 4% | 0% | 1% | 2% | 3% | 0% | 4% | 0% | 4% | 0% | 3% | 0% | 3% | 1% | 3% | 1% | 2% | 0% | 2% | 3%  |
| L  | 5% | 1% | 3% | 1% | 2% | 1% | 2% | 2% | 3% | 0% | 2% | 1% | 3% | 0% | 4% | 1% | 3% | 1% | 1% | 1% | 3% | 1% | 1% | 3%  |
| M  | 3% | 1% | 1% | 1% | 4% | 1% | 3% | 2% | 3% | 1% | 4% | 2% | 3% | 0% | 3% | 2% | 1% | 3% | 2% | 1% | 4% | 2% | 3% | 2%  |
| N  | 5% | 0% | 1% | 1% | 3% | 2% | 3% | 2% | 2% | 2% | 1% | 3% | 2% | 2% | 1% | 3% | 0% | 3% | 0% | 2% | 5% | 1% | 3% | 1%  |
| O  | 5% | 2% | 1% | 2% | 2% | 2% | 2% | 2% | 2% | 2% | 1% | 3% | 0% | 3% | 1% | 4% | 1% | 3% | 1% | 3% | 3% | 1% | 3% | 1%  |
| P  | 3% | 4% | 2% | 4% | 1% | 3% | 0% | 2% | 0% | 2% | 1% | 2% | 1% | 2% | 0% | 4% | 2% | 5% | 1% | 4% | 1% | 4% | 2% | 3%  |
| Q  | 6% | 0% | 1% | 2% | 2% | 3% | 3% | 2% | 2% | 3% | 2% | 1% | 3% | 1% | 1% | 2% | 2% | 3% | 0% | 3% | 3% | 2% | 4% | 2%  |
| R  | 5% | 0% | 0% | 4% | 3% | 2% | 2% | 1% | 2% | 3% | 0% | 3% | 2% | 4% | 1% | 3% | 1% | 2% | 1% | 3% | 4% | 0% | 2% | 2%  |
| S  | 7% | 3% | 2% | 1% | 3% | 1% | 2% | 2% | 1% | 2% | 2% | 1% | 4% | 1% | 3% | 3% | 2% | 1% | 2% | 1% | 4% | 0% | 2% | 2%  |
| T  | 3% | 2% | 3% | 1% | 3% | 1% | 2% | 2% | 0% | 1% | 3% | 0% | 2% | 1% | 3% | 2% | 1% | 2% | 1% | 1% | 4% | 1% | 2% | 3%  |
| U  | 7% | 2% | 6% | 1% | 5% | 1% | 5% | 1% | 4% | 0% | 6% | 1% | 4% | 0% | 4% | 1% | 3% | 2% | 1% | 0% | 5% | 0% | 2% | 2%  |
| V  | 5% | 0% | 6% | 1% | 5% | 1% | 3% | 2% | 3% | 1% | 4% | 0% | 4% | 0% | 2% | 1% | 3% | 2% | 1% | 3% | 4% | 0% | 1% | 3%  |
| W  | 7% | 1% | 6% | 1% | 5% | 0% | 4% | 2% | 2% | 0% | 5% | 1% | 2% | 1% | 3% | 2% | 0% | 1% | 2% | 1% | 3% | 2% | 0% | 4%  |
| X  | 4% | 3% | 4% | 1% | 4% | 0% | 3% | 1% | 2% | 1% | 4% | 2% | 0% | 3% | 2% | 3% | 0% | 2% | 2% | 2% | 2% | 2% | 0% | 3%  |
| Y  | 9% | 2% | 5% | 2% | 7% | 2% | 4% | 1% | 5% | 2% | 5% | 1% | 3% | 2% | 3% | 1% | 3% | 1% | 5% | 0% | 4% | 1% | 0% | 2%  |
| Z  | 6% | 0% | 4% | 0% | 6% | 1% | 4% | 1% | 5% | 1% | 4% | 2% | 2% | 1% | 3% | 1% | 2% | 1% | 3% | 0% | 3% | 1% | 1% | 1%  |
| AA | 6% | 1% | 5% | 0% | 5% | 2% | 5% | 2% | 6% | 0% | 5% | 1% | 2% | 1% | 4% | 0% | 3% | 1% | 5% | 1% | 2% | 0% | 2% | 1%  |
| AB | 6% | 2% | 5% | 1% | 5% | 1% | 4% | 1% | 4% | 1% | 4% | 0% | 2% | 0% | 3% | 1% | 4% | 1% | 4% | 3% | 2% | 1% | 2% | 1%  |
| AC | 4% | 1% | 3% | 0% | 5% | 1% | 4% | 1% | 4% | 0% | 3% | 2% | 1% | 1% | 3% | 3% | 2% | 0% | 2% | 2% | 2% | 1% | 2% | 2%  |
| AD | 3% | 0% | 2% | 1% | 2% | 0% | 3% | 2% | 2% | 3% | 1% | 3% | 1% | 4% | 0% | 3% | 1% | 2% | 0% | 2% | 2% | 2% | 1% | 2%  |
| AE | 2% | 2% | 2% | 3% | 1% | 0% | 2% | 3% | 0% | 3% | 1% | 3% | 2% | 4% | 0% | 4% | 1% | 2% | 1% | 3% | 1% | 3% | 0% | 3%  |
| AF | 2% | 3% | 1% | 4% | 1% | 3% | 1% | 3% | 2% | 3% | 1% | 4% | 1% | 4% | 0% | 5% | 1% | 5% | 3% | 7% | 5% | 9% | 7% | 13% |

Figure 8

Average deviation over plate 1: 3%
Percentage deviation per well - plate 1:

|    | 25  | 26  | 27 | 28 | 29 | 30 | 31 | 32 | 33 | 34 | 35 | 36 | 37 | 38 | 39 | 40 | 41 | 42 | 43 | 44 | 45 | 46 | 47 | 48 |
|----|-----|-----|----|----|----|----|----|----|----|----|----|----|----|----|----|----|----|----|----|----|----|----|----|----|
| A  | 5%  | 7%  | 2% | 7% | 1% | 5% | 0% | 3% | 3% | 3% | 0% | 4% | 0% | 3% | 0% | 5% | 0% | 2% | 4% | 1% | 3% | 2% | 4% | 1% |
| B  | 1%  | 3%  | 1% | 3% | 3% | 2% | 1% | 3% | 1% | 3% | 1% | 4% | 1% | 3% | 1% | 2% | 1% | 1% | 3% | 0% | 3% | 1% | 3% | 0% |
| C  | 3%  | 2%  | 2% | 2% | 3% | 0% | 3% | 2% | 1% | 2% | 2% | 1% | 1% | 0% | 3% | 0% | 2% | 1% | 2% | 1% | 2% | 1% | 4% | 1% |
| D  | 3%  | 2%  | 2% | 1% | 3% | 1% | 4% | 0% | 3% | 2% | 2% | 1% | 2% | 1% | 3% | 1% | 2% | 0% | 2% | 1% | 2% | 0% | 3% | 0% |
| E  | 5%  | 0%  | 5% | 0% | 5% | 2% | 6% | 1% | 5% | 1% | 5% | 1% | 5% | 1% | 4% | 1% | 4% | 0% | 5% | 1% | 5% | 3% | 6% | 1% |
| F  | 4%  | 0%  | 3% | 0% | 6% | 1% | 3% | 1% | 4% | 0% | 3% | 0% | 4% | 1% | 3% | 0% | 4% | 1% | 4% | 0% | 5% | 0% | 4% | 3% |
| G  | 2%  | 1%  | 4% | 1% | 3% | 1% | 3% | 2% | 3% | 1% | 1% | 3% | 3% | 1% | 3% | 1% | 2% | 1% | 4% | 0% | 3% | 1% | 3% | 0% |
| H  | 1%  | 2%  | 2% | 2% | 3% | 0% | 2% | 3% | 0% | 4% | 1% | 3% | 1% | 2% | 0% | 2% | 3% | 1% | 3% | 1% | 3% | 3% | 2% | 2% |
| I  | 2%  | 1%  | 3% | 0% | 4% | 0% | 3% | 3% | 2% | 3% | 1% | 2% | 4% | 0% | 3% | 2% | 4% | 0% | 4% | 1% | 3% | 0% | 3% | 2% |
| J  | 0%  | 2%  | 2% | 2% | 3% | 1% | 2% | 2% | 2% | 2% | 1% | 3% | 2% | 2% | 1% | 3% | 2% | 3% | 2% | 2% | 3% | 1% | 2% | 1% |
| K  | 1%  | 1%  | 3% | 1% | 2% | 3% | 2% | 2% | 3% | 1% | 2% | 2% | 2% | 1% | 2% | 4% | 0% | 3% | 1% | 2% | 2% | 1% | 3% | 1% |
| L  | 2%  | 1%  | 3% | 1% | 3% | 4% | 1% | 2% | 1% | 1% | 1% | 2% | 0% | 2% | 1% | 2% | 0% | 3% | 0% | 4% | 1% | 1% | 2% | 2% |
| M  | 3%  | 1%  | 3% | 1% | 3% | 2% | 1% | 4% | 1% | 2% | 1% | 4% | 0% | 4% | 0% | 3% | 0% | 2% | 1% | 3% | 1% | 2% | 2% | 3% |
| N  | 3%  | 0%  | 3% | 1% | 2% | 3% | 1% | 4% | 2% | 3% | 0% | 4% | 1% | 4% | 1% | 3% | 1% | 4% | 2% | 5% | 1% | 3% | 0% | 0% |
| O  | 2%  | 1%  | 4% | 1% | 0% | 3% | 0% | 5% | 1% | 4% | 2% | 5% | 4% | 5% | 1% | 4% | 2% | 5% | 1% | 6% | 1% | 5% | 1% | 1% |
| P  | 0%  | 3%  | 0% | 4% | 1% | 3% | 1% | 4% | 1% | 2% | 1% | 3% | 1% | 4% | 1% | 3% | 1% | 3% | 2% | 6% | 2% | 6% | 4% | 5% |
| Q  | 3%  | 1%  | 1% | 2% | 3% | 4% | 1% | 3% | 0% | 4% | 1% | 3% | 2% | 3% | 2% | 3% | 0% | 4% | 1% | 7% | 2% | 5% | 2% | 9% |
| R  | 2%  | 1%  | 1% | 2% | 1% | 3% | 0% | 3% | 1% | 4% | 1% | 4% | 1% | 3% | 0% | 3% | 0% | 4% | 1% | 7% | 5% | 7% | 5% | 3% |
| S  | 2%  | 0%  | 3% | 1% | 2% | 2% | 2% | 4% | 1% | 3% | 1% | 4% | 2% | 2% | 1% | 3% | 2% | 3% | 1% | 5% | 7% | 7% | 2% | 5% |
| T  | 1%  | 0%  | 1% | 1% | 1% | 4% | 1% | 4% | 0% | 3% | 1% | 3% | 1% | 2% | 1% | 2% | 2% | 3% | 0% | 5% | 4% | 7% | 3% | 7% |
| U  | 3%  | 2%  | 2% | 0% | 2% | 4% | 1% | 2% | 2% | 1% | 0% | 3% | 2% | 2% | 2% | 3% | 0% | 3% | 1% | 4% | 0% | 1% | 1% | 2% |
| V  | 2%  | 3%  | 2% | 2% | 3% | 3% | 0% | 2% | 2% | 1% | 0% | 2% | 2% | 3% | 0% | 4% | 0% | 6% | 2% | 4% | 0% | 3% | 1% | 2% |
| W  | 2%  | 3%  | 2% | 2% | 2% | 2% | 1% | 3% | 3% | 1% | 1% | 2% | 0% | 4% | 2% | 3% | 1% | 4% | 0% | 4% | 2% | 3% | 2% | 1% |
| X  | 2%  | 3%  | 1% | 1% | 3% | 1% | 1% | 3% | 0% | 3% | 1% | 4% | 0% | 4% | 1% | 4% | 1% | 4% | 1% | 5% | 1% | 3% | 2% | 4% |
| Y  | 2%  | 2%  | 2% | 1% | 5% | 0% | 3% | 1% | 2% | 2% | 0% | 4% | 1% | 1% | 2% | 2% | 2% | 2% | 1% | 3% | 1% | 2% | 3% | 1% |
| Z  | 3%  | 2%  | 2% | 1% | 3% | 1% | 1% | 2% | 3% | 1% | 0% | 4% | 0% | 3% | 1% | 2% | 1% | 4% | 0% | 4% | 1% | 2% | 1% | 3% |
| AA | 3%  | 1%  | 3% | 1% | 2% | 1% | 2% | 2% | 4% | 1% | 2% | 2% | 0% | 1% | 2% | 1% | 1% | 2% | 1% | 5% | 0% | 2% | 2% | 3% |
| AB | 3%  | 2%  | 3% | 1% | 1% | 0% | 2% | 3% | 2% | 2% | 1% | 3% | 0% | 2% | 2% | 2% | 1% | 4% | 3% | 5% | 1% | 1% | 1% | 3% |
| AC | 2%  | 1%  | 2% | 3% | 1% | 3% | 1% | 4% | 1% | 3% | 1% | 3% | 1% | 2% | 1% | 3% | 0% | 4% | 0% | 3% | 1% | 1% | 1% | 3% |
| AD | 0%  | 3%  | 0% | 4% | 1% | 2% | 0% | 4% | 0% | 4% | 0% | 4% | 1% | 4% | 0% | 4% | 1% | 4% | 1% | 5% | 1% | 4% | 0% | 3% |
| AE | 2%  | 5%  | 1% | 4% | 1% | 3% | 1% | 5% | 2% | 3% | 1% | 6% | 3% | 5% | 2% | 6% | 2% | 4% | 1% | 4% | 3% | 4% | 0% | 6% |
| AF | 12% | 10% | 5% | 9% | 7% | 7% | 2% | 5% | 1% | 3% | 1% | 5% | 1% | 4% | 2% | 6% | 3% | 6% | 2% | 7% | 4% | 5% | 1% | 4% |

Figure 8 (Cont.)

Average deviation over plate 2: 5%
Percentage deviation per well - plate 2:

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | 3% | 1% | 4% | 1% | 4% | 1% | 3% | 4% | 0% | 3% | 2% | 5% | 1% | 3% | 1% | 3% | 0% | 3% | 2% | 7% | 3% | 7% | 5% | 12% |
| B | 2% | 2% | 1% | 2% | 3% | 1% | 2% | 2% | 1% | 2% | 0% | 4% | 0% | 3% | 1% | 4% | 0% | 2% | 0% | 4% | 1% | 3% | 1% | 3% |
| C | 4% | 1% | 2% | 2% | 1% | 3% | 3% | 2% | 3% | 0% | 3% | 3% | 1% | 2% | 2% | 4% | 2% | 1% | 2% | 2% | 1% | 2% | 2% | 1% |
| D | 3% | 1% | 3% | 2% | 1% | 3% | 2% | 1% | 4% | 0% | 4% | 1% | 3% | 1% | 4% | 1% | 4% | 0% | 4% | 2% | 2% | 1% | 3% | 1% |
| E | 5% | 0% | 3% | 0% | 4% | 1% | 5% | 0% | 5% | 0% | 5% | 0% | 5% | 1% | 2% | 2% | 5% | 1% | 4% | 0% | 4% | 1% | 3% | 1% |
| F | 4% | 0% | 4% | 1% | 2% | 1% | 3% | 0% | 3% | 1% | 5% | 0% | 2% | 0% | 0% | 1% | 3% | 0% | 4% | 0% | 4% | 1% | 2% | 1% |
| G | 6% | 1% | 3% | 1% | 3% | 0% | 3% | 1% | 3% | 0% | 3% | 1% | 0% | 3% | 1% | 3% | 1% | 1% | 2% | 2% | 2% | 1% | 2% | 3% |
| H | 4% | 2% | 2% | 3% | 2% | 1% | 4% | 2% | 2% | 1% | 3% | 3% | 0% | 6% | 3% | 5% | 1% | 4% | 2% | 2% | 1% | 2% | 3% | 3% |
| I | 4% | 2% | 2% | 2% | 3% | 0% | 3% | 1% | 3% | 1% | 2% | 2% | 3% | 2% | 2% | 1% | 1% | 2% | 2% | 1% | 3% | 1% | 2% | 3% |
| J | 5% | 0% | 2% | 1% | 1% | 0% | 1% | 2% | 2% | 2% | 2% | 3% | 2% | 1% | 3% | 1% | 3% | 1% | 2% | 2% | 1% | 2% | 0% | 5% |
| K | 5% | 0% | 3% | 2% | 3% | 0% | 1% | 2% | 2% | 1% | 2% | 2% | 3% | 1% | 4% | 1% | 3% | 0% | 3% | 2% | 2% | 1% | 2% | 3% |
| L | 3% | 1% | 2% | 2% | 1% | 1% | 5% | 1% | 2% | 2% | 2% | 2% | 1% | 1% | 4% | 0% | 3% | 1% | 4% | 1% | 3% | 1% | 3% | 3% |
| M | 2% | 0% | 0% | 2% | 2% | 2% | 5% | 1% | 1% | 1% | 1% | 3% | 1% | 1% | 2% | 3% | 1% | 3% | 2% | 1% | 3% | 2% | 2% | 2% |
| N | 4% | 1% | 1% | 3% | 0% | 2% | 3% | 2% | 0% | 2% | 2% | 4% | 1% | 3% | 0% | 3% | 2% | 2% | 2% | 1% | 3% | 0% | 2% | 1% |
| O | 4% | 4% | 1% | 4% | 1% | 2% | 0% | 2% | 1% | 3% | 2% | 4% | 0% | 2% | 0% | 4% | 1% | 3% | 1% | 4% | 3% | 0% | 3% | 1% |
| P | 1% | 5% | 2% | 5% | 1% | 2% | 2% | 3% | 0% | 3% | 1% | 4% | 2% | 3% | 1% | 4% | 0% | 4% | 0% | 5% | 1% | 4% | 1% | 2% |
| Q | 5% | 1% | 0% | 2% | 2% | 3% | 2% | 3% | 1% | 2% | 2% | 2% | 2% | 1% | 2% | 2% | 3% | 2% | 0% | 3% | 2% | 2% | 3% | 1% |
| R | 5% | 1% | 2% | 4% | 2% | 2% | 0% | 2% | 1% | 1% | 2% | 3% | 1% | 2% | 2% | 2% | 2% | 1% | 2% | 2% | 3% | 1% | 4% | 1% |
| S | 5% | 1% | 1% | 2% | 3% | 1% | 1% | 2% | 1% | 1% | 2% | 3% | 4% | 0% | 3% | 3% | 2% | 0% | 4% | 0% | 3% | 1% | 2% | 2% |
| T | 4% | 0% | 4% | 1% | 3% | 1% | 2% | 2% | 0% | 1% | 2% | 1% | 2% | 0% | 4% | 2% | 1% | 3% | 3% | 0% | 4% | 0% | 2% | 3% |
| U | 6% | 0% | 5% | 0% | 5% | 0% | 4% | 0% | 3% | 0% | 3% | 1% | 4% | 1% | 4% | 0% | 5% | 1% | 2% | 1% | 5% | 0% | 3% | 1% |
| V | 5% | 1% | 5% | 0% | 4% | 0% | 3% | 1% | 3% | 0% | 4% | 1% | 4% | 0% | 3% | 0% | 3% | 1% | 1% | 1% | 4% | 0% | 2% | 3% |
| W | 5% | 1% | 5% | 1% | 3% | 1% | 4% | 1% | 4% | 0% | 3% | 2% | 3% | 0% | 3% | 1% | 2% | 2% | 3% | 2% | 2% | 1% | 2% | 4% |
| X | 4% | 1% | 5% | 2% | 2% | 0% | 3% | 1% | 2% | 1% | 3% | 3% | 1% | 2% | 3% | 2% | 3% | 1% | 3% | 2% | 3% | 1% | 2% | 3% |
| Y | 5% | 1% | 5% | 1% | 6% | 2% | 3% | 0% | 4% | 1% | 4% | 1% | 2% | 1% | 3% | 1% | 4% | 1% | 5% | 0% | 5% | 1% | 2% | 1% |
| Z | 4% | 0% | 4% | 0% | 4% | 1% | 3% | 0% | 4% | 0% | 3% | 2% | 2% | 0% | 4% | 0% | 2% | 0% | 4% | 0% | 4% | 1% | 2% | 1% |
| AA | 4% | 1% | 5% | 0% | 4% | 2% | 4% | 1% | 5% | 0% | 4% | 2% | 2% | 1% | 5% | 0% | 4% | 0% | 5% | 1% | 4% | 0% | 3% | 1% |
| AB | 5% | 1% | 5% | 1% | 5% | 0% | 3% | 0% | 4% | 0% | 2% | 2% | 2% | 0% | 4% | 0% | 4% | 0% | 5% | 1% | 2% | 1% | 4% | 0% |
| AC | 3% | 0% | 3% | 0% | 5% | 1% | 4% | 0% | 3% | 1% | 2% | 3% | 1% | 1% | 2% | 2% | 4% | 1% | 2% | 0% | 2% | 1% | 2% | 0% |
| AD | 3% | 0% | 2% | 1% | 3% | 0% | 4% | 2% | 1% | 3% | 0% | 4% | 1% | 5% | 1% | 2% | 0% | 1% | 3% | 1% | 2% | 1% | 1% | 1% |
| AE | 5% | 2% | 2% | 2% | 3% | 1% | 2% | 5% | 1% | 4% | 1% | 5% | 0% | 3% | 2% | 3% | 1% | 3% | 1% | 3% | 0% | 3% | 0% | 3% |
| AF | 6% | 2% | 2% | 4% | 0% | 3% | 2% | 4% | 2% | 3% | 3% | 4% | 2% | 3% | 2% | 4% | 0% | 4% | 2% | 7% | 5% | 8% | 5% | 12% |

Figure 9

Average deviation over plate 2: 5%
Percentage deviation per well - plate 2:

|    | 25  | 26  | 27 | 28 | 29 | 30 | 31 | 32 | 33 | 34 | 35 | 36 | 37 | 38 | 39 | 40 | 41 | 42 | 43 | 44 | 45 | 46 | 47   | 48   |
|----|-----|-----|----|----|----|----|----|----|----|----|----|----|----|----|----|----|----|----|----|----|----|----|------|------|
| A  | 7%  | 8%  | 3% | 7% | 1% | 4% | 0% | 4% | 2% | 4% | 0% | 4% | 1% | 4% | 0% | 5% | 0% | 2% | 3% | 1% | 2% | 1% | 4%   | 1%   |
| B  | 2%  | 3%  | 1% | 3% | 1% | 2% | 1% | 3% | 1% | 3% | 0% | 4% | 0% | 3% | 1% | 2% | 1% | 1% | 3% | 1% | 2% | 0% | 3%   | 1%   |
| C  | 3%  | 2%  | 1% | 2% | 3% | 0% | 3% | 1% | 3% | 2% | 1% | 3% | 1% | 1% | 4% | 1% | 2% | 1% | 2% | 2% | 1% | 3% | 4%   | 0%   |
| D  | 3%  | 1%  | 3% | 2% | 3% | 1% | 3% | 1% | 3% | 1% | 3% | 1% | 2% | 1% | 4% | 1% | 1% | 1% | 3% | 2% | 2% | 1% | 4%   | 2%   |
| E  | 4%  | 0%  | 5% | 0% | 4% | 1% | 5% | 1% | 3% | 1% | 4% | 0% | 5% | 1% | 3% | 0% | 2% | 1% | 3% | 0% | 4% | 3% | 5%   | 5%   |
| F  | 4%  | 0%  | 4% | 0% | 4% | 0% | 3% | 0% | 2% | 1% | 2% | 1% | 5% | 0% | 4% | 1% | 3% | 1% | 3% | 1% | 4% | 1% | 4%   | 4%   |
| G  | 3%  | 1%  | 3% | 1% | 3% | 0% | 3% | 2% | 0% | 1% | 2% | 4% | 3% | 1% | 4% | 0% | 3% | 0% | 4% | 1% | 3% | 0% | 4%   | 1%   |
| H  | 1%  | 3%  | 3% | 2% | 2% | 3% | 2% | 4% | 1% | 3% | 1% | 5% | 2% | 2% | 2% | 2% | 2% | 1% | 3% | 1% | 3% | 1% | 4%   | 2%   |
| I  | 2%  | 3%  | 3% | 1% | 3% | 1% | 2% | 3% | 2% | 3% | 1% | 2% | 3% | 0% | 3% | 1% | 4% | 1% | 4% | 1% | 3% | 0% | 4%   | 2%   |
| J  | 1%  | 3%  | 1% | 2% | 2% | 2% | 2% | 3% | 1% | 1% | 2% | 3% | 1% | 2% | 3% | 1% | 1% | 2% | 2% | 3% | 3% | 1% | 4%   | 2%   |
| K  | 0%  | 4%  | 3% | 1% | 2% | 2% | 3% | 4% | 3% | 1% | 1% | 2% | 2% | 0% | 2% | 2% | 0% | 2% | 2% | 3% | 2% | 0% | 3%   | 2%   |
| L  | 1%  | 2%  | 4% | 1% | 2% | 3% | 2% | 1% | 2% | 1% | 2% | 2% | 1% | 2% | 2% | 2% | 1% | 3% | 2% | 4% | 2% | 0% | 5%   | 0%   |
| M  | 2%  | 1%  | 2% | 1% | 2% | 1% | 0% | 4% | 2% | 1% | 2% | 3% | 1% | 3% | 0% | 3% | 1% | 2% | 1% | 4% | 1% | 0% | 4%   | 2%   |
| N  | 2%  | 0%  | 4% | 2% | 0% | 1% | 2% | 4% | 1% | 2% | 1% | 2% | 0% | 3% | 1% | 3% | 1% | 2% | 1% | 4% | 0% | 1% | 2%   | 2%   |
| O  | 2%  | 1%  | 3% | 2% | 0% | 2% | 1% | 4% | 0% | 4% | 1% | 4% | 1% | 4% | 1% | 3% | 2% | 4% | 1% | 5% | 0% | 2% | 2%   | 2%   |
| P  | 2%  | 2%  | 1% | 5% | 1% | 3% | 2% | 4% | 1% | 2% | 2% | 2% | 0% | 3% | 2% | 3% | 1% | 3% | 0% | 6% | 1% | 5% | 1%   | 3%   |
| Q  | 3%  | 0%  | 1% | 3% | 1% | 4% | 2% | 3% | 1% | 3% | 1% | 3% | 3% | 1% | 2% | 2% | 1% | 4% | 1% | 5% | 3% | 5% | 2%   | 2%   |
| R  | 2%  | 1%  | 1% | 2% | 1% | 2% | 1% | 5% | 1% | 3% | 0% | 3% | 1% | 2% | 1% | 1% | 1% | 3% | 1% | 5% | 5% | 6% | 2%   | 3%   |
| S  | 1%  | 0%  | 3% | 1% | 2% | 2% | 3% | 5% | 0% | 2% | 2% | 3% | 2% | 1% | 2% | 0% | 0% | 3% | 0% | 5% | 7% | 6% | 42%  | 3%   |
| T  | 1%  | 1%  | 2% | 3% | 1% | 2% | 2% | 4% | 1% | 2% | 3% | 3% | 2% | 2% | 2% | 2% | 0% | 3% | 2% | 5% | 3% | 6% | 100% | 100% |
| U  | 3%  | 2%  | 3% | 0% | 2% | 3% | 1% | 1% | 1% | 0% | 2% | 2% | 3% | 2% | 2% | 2% | 1% | 3% | 1% | 2% | 1% | 1% | 4%   | 1%   |
| V  | 2%  | 2%  | 2% | 2% | 2% | 3% | 1% | 1% | 2% | 1% | 2% | 2% | 3% | 1% | 2% | 2% | 0% | 4% | 0% | 4% | 1% | 2% | 3%   | 2%   |
| W  | 2%  | 2%  | 2% | 2% | 3% | 1% | 2% | 3% | 3% | 0% | 2% | 2% | 1% | 2% | 2% | 2% | 0% | 3% | 1% | 4% | 1% | 2% | 2%   | 0%   |
| X  | 1%  | 2%  | 2% | 2% | 3% | 1% | 3% | 3% | 2% | 1% | 1% | 3% | 1% | 4% | 2% | 2% | 0% | 3% | 1% | 4% | 1% | 2% | 4%   | 2%   |
| Y  | 2%  | 1%  | 3% | 0% | 5% | 1% | 5% | 2% | 3% | 0% | 2% | 2% | 2% | 0% | 2% | 1% | 1% | 2% | 1% | 2% | 2% | 0% | 4%   | 1%   |
| Z  | 2%  | 2%  | 3% | 2% | 4% | 1% | 4% | 1% | 3% | 1% | 2% | 2% | 0% | 1% | 2% | 1% | 0% | 2% | 0% | 4% | 1% | 1% | 4%   | 0%   |
| AA | 2%  | 1%  | 4% | 1% | 3% | 1% | 4% | 1% | 4% | 0% | 3% | 1% | 1% | 0% | 2% | 1% | 1% | 1% | 3% | 3% | 1% | 1% | 4%   | 1%   |
| AB | 3%  | 2%  | 3% | 1% | 2% | 1% | 3% | 3% | 3% | 1% | 4% | 2% | 1% | 1% | 4% | 2% | 0% | 2% | 0% | 4% | 2% | 0% | 4%   | 1%   |
| AC | 3%  | 2%  | 1% | 2% | 3% | 3% | 2% | 4% | 0% | 2% | 2% | 3% | 1% | 1% | 3% | 3% | 1% | 3% | 0% | 2% | 2% | 1% | 2%   | 1%   |
| AD | 1%  | 3%  | 1% | 3% | 1% | 3% | 1% | 3% | 1% | 2% | 0% | 5% | 0% | 2% | 1% | 4% | 1% | 2% | 1% | 3% | 0% | 1% | 1%   | 1%   |
| AE | 1%  | 2%  | 1% | 3% | 2% | 3% | 0% | 5% | 1% | 3% | 1% | 5% | 3% | 2% | 0% | 7% | 1% | 2% | 0% | 3% | 1% | 2% | 2%   | 4%   |
| AF | 11% | 10% | 4% | 8% | 6% | 7% | 1% | 6% | 1% | 3% | 0% | 4% | 0% | 1% | 2% | 6% | 3% | 5% | 2% | 5% | 2% | 2% | 3%   | 1%   |

Figure 9 (Cont)

METHOD AND APPARATUS FOR DISPENSING A LIQUID INTO A SERIES OF WELLS

CROSS REFERENCE TO RELATED APPLICATIONS

This application is the national stage of Application No. PCT/EP01/02808, filed Mar. 8, 2001 which application claims priority from EP 00200813.4, filed Mar. 8, 2000, incorporated herein by reference.

The present invention relates to a method and apparatus for dispensing a predetermined volume of fluid from a reservoir, through a fluid outlet in fluid communication with said reservoir, onto a support and more in particular into each well of at least one series of wells.

The invention is also related to a support and more in particular to a micro titer plate in which the wells are filled using the method and/or the apparatus of the invention.

In a first aspect the invention is related to a method for dispensing a predetermined volume of a fluid, such as a chemical or biological reagent or any other fluid, from a reservoir, through a fluid outlet in fluid communication with said reservoir, into each well of at least one series of wells, such that the volume in each of said well is substantially equal, whereby the method comprises a dispensing mode and a non-dispensing mode.

The invention is of particular use for providing a dispensing technique for high throughput screening (HTS) purposes. In general HTS can be defined as the use of miniaturized, robotics-based technology to screen large compound libraries against an isolated target protein, cell or tissue in order to identify compounds that may be potential new drugs. High-throughput screening commonly depends on the development of a quantitative, pharmacologically relevant assay for the identified target, which can then be reproduced across a large number of samples with the use of specific supports. Series of wells are usually comprised in multi-well or so-called micro titer plates. Such multi-well plates are currently used with a number of different applications, such as the screening of compounds in drug discovery programs, performing cell-based assays, performing synthesis reactions in combinatorial chemistry, performing polymerase chain reactions, etc.

Typically, high-throughput screening supports have relied on 96-well plates as the standard, although higher-density formats (384, 864, 1536, 9600 etc.) are possible. In general, due to automation and robotics a plurality of wells of the standard 96 wells is used. These supports, commonly known as micro titer plates are designed for medical or other laboratories are conventionally constructed from a piece of plastic containing a plurality of wells.

Traditionally, dosing of fluids in the wells of multi-well plates requires quantities of fluid to be taken up in one or more pipettes, such as piëzo-electric pipettes, and their release into the wells of said multi-well plates. Alternatively, metered quantities of the fluid are each time pumped through a nozzle in the successive wells. These pipettes or nozzles need to be positioned first on top of or into the wells of the multi-well plate. Next, the fluid is ejected or droplet per droplet dispensed. Subsequently, these pipettes or nozzles need to be positioned above or near these wells. As a result, a major drawback of these methods known in the art is that they are only suited for the handling of multi-well plates with a limited number of wells (in particular 96-well standard micro titer plates) but not for multi-well plates having a larger number of wells, such as, for example, 384, 864, 1536, 3456, 3840 or 9600 wells. Indeed, filling such a number of wells using art-known methods takes too much time and is hence inefficient.

Several automated dispensing techniques for dispensing fluids are known.

U.S. Pat. No. 6,063,339, which document was published after the priority date of the present invention discloses a method and apparatus for dispensing droplets in various desired patterns onto a support using a method according to the preamble of claim 1. The disclosed method is suitable for dispensing droplets being discrete separate volumes. The dispensed fluid may contain particles such as molecules, cells, proteins, etc. elements or particles which may be damaged when undergoing the droplet formation.

EP-A-0 937 502 discloses a method and device for handling sample plates in which a dosing equipment is provided for dispensing. This document proposes a dispensing method in which the sample plate is moved with respect to a number of dosing tips. A main object of the present invention is to provide a method and apparatus able to dispense a precise volume in each well of a support. Movement of the support however may result in inaccurate volumes remaining in each well. Furthermore the multitude of dosing tips may, due to variations in material, fabrication, wear, dimensions etc., cause differences in the dispensed volumes.

Therefore, it is an object of a first aspect of the present invention to provide a new method that enables the dispensing of a predetermined and accurate volume of a fluid into each well of a series of wells at high speed.

The method according to the invention is characterised in that in the dispensing mode the fluid is dispensed at a continuous uninterrupted flow from a moving fluid outlet into a series of wells. For adding a predetermined volume of fluid into each well said fluid outlet is moved relatively to said series of wells so that it passes over said series of wells and during this passing said predetermined volume of fluid is dispensed into each well of said series of wells. The flow pattern of the fluid is a continuous uninterrupted flow, which increases the bioviability of the dispensed fluid in contrast to droplets dispension.

According to a preferred embodiment the movement of the fluid outlet relatively to said series of wells has a constant relative speed with respect to the series of wells when passing over said series of wells. A main object is to provide an very accurate dispensing method wherein the same volume is dispensed in each well of the support. Due to the combination of a continuous uninterrupted flow pattern and a constant relative speed of the flow outlet a same volume is obtained into each well of a series of wells.

According to the invention it has been found that the speed at which the wells of a multi-well plate can be filled is limited by the mechanical movement of the fluid outlet over the series of wells. In the prior art methods, this movement is indeed to be stopped each time when passing over one well. In the method according to the first aspect of the present invention, the fluid outlet is passed in a continuous movement over the series of wells. The velocity at which the outlet may pass over the series of wells is therefore no longer limited by the limitations imposed by a discontinuous movement of the fluid outlet.

The present invention has found that the required quantities of fluid can be obtained in the different wells without interrupting the flow of fluid out of the fluid outlet. An advantage of this preferred embodiment is clearly that a less complicated dispensing system is required since the flow of fluid has no longer to be interrupted at a rather high frequency and since no control system is required to synchronise the interruptions of the fluid flow with the movement over the series of wells.

As elucidated above it has moreover been found that dispensing very small amounts of fluid in the different wells by pulsed flow of this fluid may have deteriorative effects on the fluid, in particular when this fluid contains biological material such as living cells or organisms or macromolecules.

The present invention offers a solution to this problem which consists in that for adding said predetermined volume of fluid into each well of said series of wells, said fluid outlet is moved relatively to said series of wells so that it passes over said series of wells and during this passing an uninterrupted flow of said fluid is dispensed out of the fluid outlet.

As set forth above, the required quantities of fluid can indeed also be obtained in the different wells without interrupting the flow of fluid out of the fluid outlet. In this way, there is a smaller risk of damaging biological or other sensitive material which may be contained in the fluid. Although preference is given also in this aspect of the invention to a continuous movement of the fluid outlet relative to the series of wells, one could possibly stop the movement of the outlet above each well, in particular when the fluid is dispensed at a small flow rate and a relatively large volume of fluid is to be added into each well.

In a preferred embodiment of the method according to both aspects of the invention, the fluid is dispensed uninterruptedly at a substantially constant flow rate out of said outlet moved into a straight line when it passes over said series of wells. Preferably, the fluid outlet is moved at a substantially constant speed relative to the series of wells when it passes over the wells. In this way a constant volume of fluid is achieved in each well.

Another aspect of the present invention is the particular use of a non-dispensing mode. Said non-dispensing mode is preferably used when passing from a first series to a second series of wells. As should be understood a series of wells is an aligned set of wells consisting essentially of one row or one column of wells. A support essentially consists of a number of straight lined columns or rows being aligned in parallel to each other. In order to fill all the wells of a support the fluid outlet should be moved from a position at the end of a first filled series to a position at the beginning of another series to be filled.

The present invention found that an inaccurate speed pattern can arise when the fluid outlet is moved in bends or curved lines. A movement of the fluid outlet into straight lines is therefore preferred in the dispensing mode. In order to be able to obtain a constant relative speed of the fluid outlet in the straight dispensing mode, said outlet is closed when a movement in a bend or curved line needs to be made. A movement in a bend or curved line is always a necessity when turning from a first filled series to a further to be filled series. This movement is made in the non-dispensing mode.

Further advantages of the dispensing and the non-dispensing mode are included in the sub-claims.

In a second aspect the invention is related to a support, in particular to a micro titer plate constructed preferably from a hydrophobic, and more in particular from a plastic material containing a plurality of parallel extending series of wells forming an array of wells, whereby the number of wells can for example be 96 organized as an array of twelve series of eight wells or any other number of wells such as 384, 864, 1536, 9600 containing a fluid dispensed in said wells by using the method according to the present invention.

As will be further analyzed hereunder the present method provides for a very accurate dispensing method whereby substantially the same volume is dispensed into each well of the support. The average difference in volume of the dispensed fluid into each well is minimal and is less than 10%, preferably about 5% or less, more preferably about 4% or less and most preferably about 3% or less.

In a third aspect the invention is also related to an apparatus for dispensing a volume of fluid from a reservoir, through a fluid outlet in fluid communication with said reservoir comprising:

a fluid outlet having an inlet and an outlet end for dispensing an uninterrupted flow of fluid originating from said reservoir onto a support comprising a series of wells, said support and/or a fluid outlet being secured in association with a table or carrier able to provide a relative X, X-Y or X-Y-Z motion between the support and the fluid outlet, and pumping means for providing an uninterrupted flow of fluid through the fluid outlet from the reservoir and a controller adapted to provide a dispensing and a non-dispensing mode, whereby the controller further is able to control the dispensing such that a substantial equal volume of fluid to be dispensed into each well during a dispensing mode is provided.

Other particularities and advantages of the invention will become apparent from the following description of some particular embodiments of the present method for adding predetermined quantities of fluid into at least one series of wells. The reference numerals used in this description relate to the annexed drawings wherein:

FIGS. 6, 7, 8 and 9 show 1536 well plates filled with the method according to the invention with their respective deviation in volume in each well.

Figure 1:
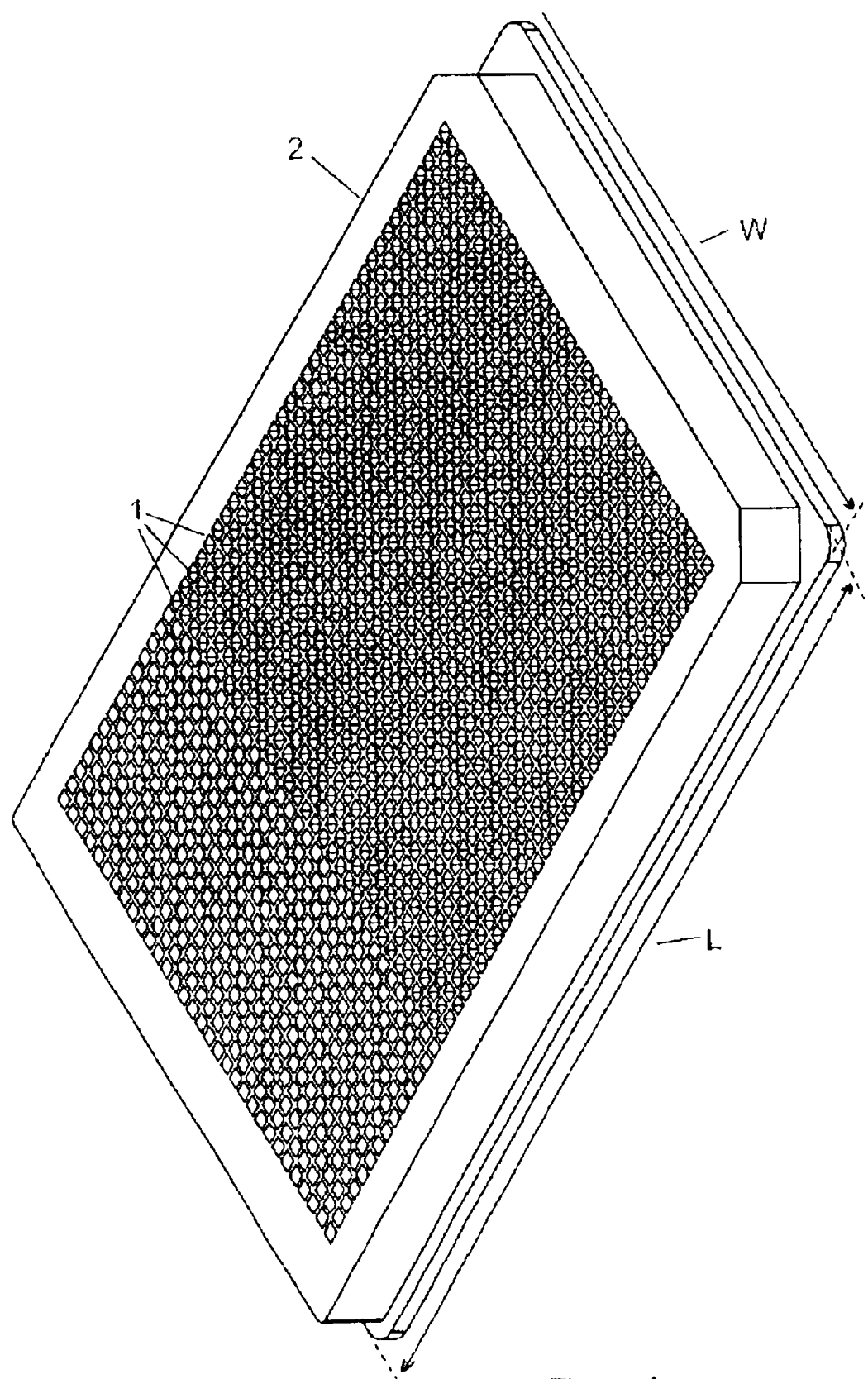
FIG. 1 shows a perspective view of a standard 1536 well plate.

As described above the present invention is based on the theoretical principle that a constant flow of fluid dispensed via a moving fluid outlet with a constant speed over a well plate will result in a constant volume applied in each well. The practical use of said principle requires the use of two modes, i.e. a first dispensing mode wherein the above principle is used along a straight line pattern of movement and a non-dispensing mode. The latter mode is used for the non-straight movement of the fluid outlet when passing from a first filled series towards a second series of wells.

The present invention relates to a new method for adding a predetermined volume of fluid into the wells 1 of a multi-well plate 2 or more generally in a series of wells 1, for example in one or more rows of a multi-well plate. The plate illustrated in FIG. 1 comprises 1536 wells (32×48) and has a standard length L of about 128 mm and a standard width W of about 86 mm. The array of wells itself has a length L of about 109 mm and a width w of about 73 mm. The area of this array is thus smaller than 100 $cm^2$. Instead of 1536 wells, the plate of these standard dimensions may contain another multiplicity of the standard 96 wells such as, for example, 384, 864, 3456, 3840, 6144 or 9600 wells.

The invention is not limited to the nature of the fluid to be added into the wells. This fluid may for example be a liquid or a so-called semi-solid medium.

In case the wells are used with the intention to screen analytes, they are first filled with said analytes for which various known techniques may be used. Subsequently, a fluid containing a so-called target is to be applied into the wells to test whether there is any analyte-target interaction. The target may in particular be composed of cells, viruses, molecules, receptors, beads or combinations thereof. One additional advantage of the second aspect of the present invention when using it for screening purposes is that there is little or no risk of harming living biological organisms, such as cells, while transferring said living organisms from the reservoir, which is in fluid communication with the outlet, to the wells in an uninterrupted flow.

In case synthesis reactions in combinatorial chemistry are performed in the series of wells, the fluid to be added may contain for instance a reagent in a particular solvent. The apparatus of the invention is however not limited to only one fluid outlet. Several fluid outlets can provide for the simultaneous dispension of two or more fluids in a single operation.

In an advantageous embodiment of the method according to the invention, the fluid is no longer separately added into the individual wells 1 by means of pipettes or by means of a pump which pumps each time a metered dose in the wells. Instead, the fluid is introduced in a series of wells 1 in a dispensing mode by dispensing an uninterrupted flow of the fluid out of a fluid outlet 3 and by simultaneously passing this fluid outlet 3, in a continuous straight lined movement with a constant speed over the series of wells 1. Obviously, when having passed over the series of wells 1, the fluid flow may be interrupted. It has been found that notwithstanding the fact that the movement of fluid outlet 3 is not stopped above each of the wells and the fluid flow is not interrupted when moving to a next well, this method still allows to achieve the required quantities of fluid in each of the wells. Compared to existing discontinuous dosing techniques, this method offers the advantage that a larger amount of wells can be filled with the required precise volume of liquid in a much shorter period of time.

Before describing the further particularities of the method according to the invention, a short description will now be given of an apparatus that is suitable for performing this method.

Figure 4:
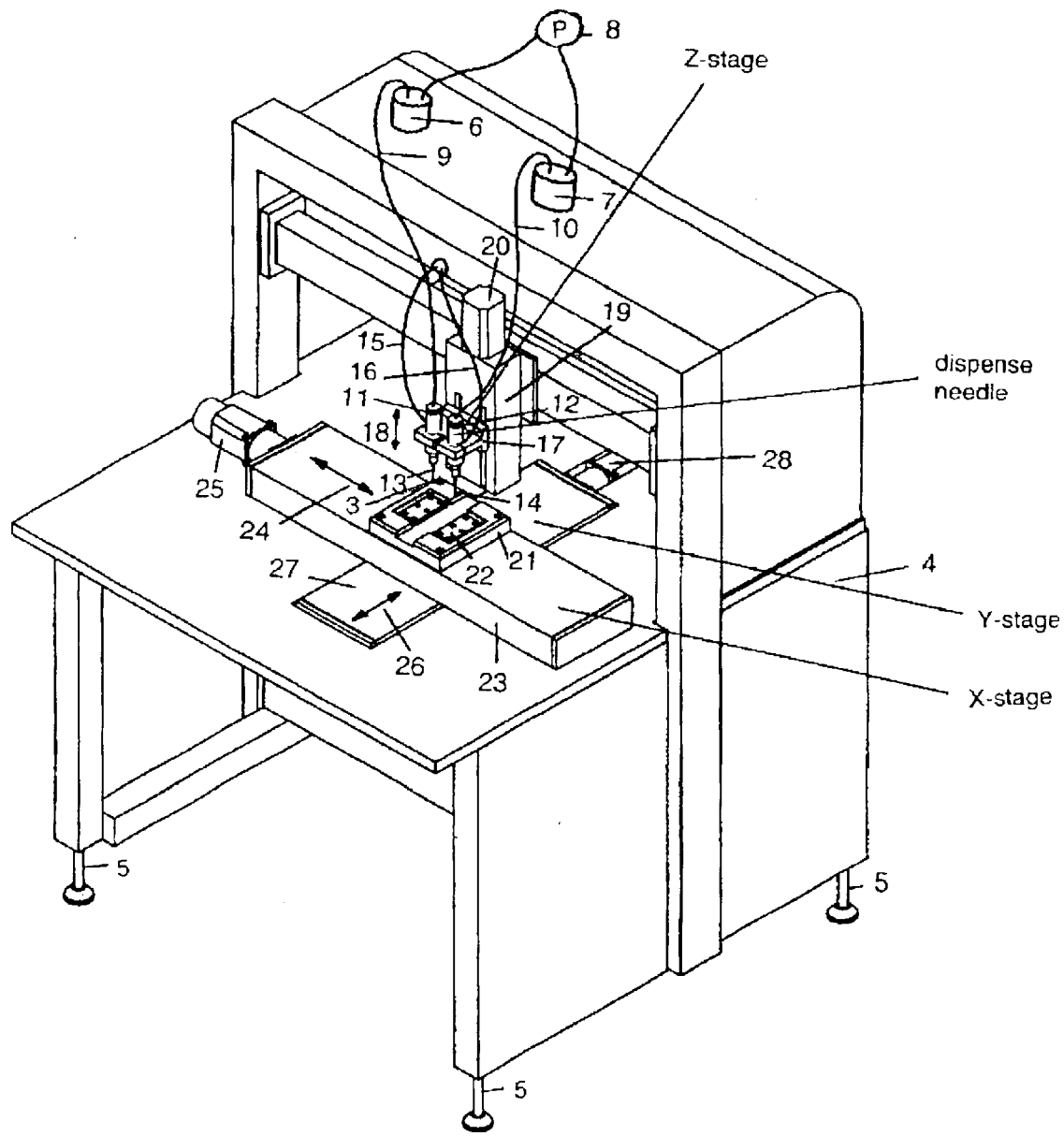
FIG. 4 shows schematically a perspective view of an apparatus that can be used for introducing the fluid in the wells of a multi-well plate.

The apparatus illustrated in FIG. 4 comprises a frame 4 supported by four legs 5. On top of the frame 4, two reservoirs 6, 7 are provided each containing a fluid to be introduced in the wells 1 of a multi-well plate. The reservoirs 6, 7 are connected on the one hand to a source of pressurized gas 8 and on the other hand, through flexible tubes 9, 10 to two fluid outlets consisting of the dispense needles 11, 12. These dispense needles 11, 12 comprise a valve, for example a so-called diaphragm valve or a piëzo-electric valve, for controlling the flow of fluid through the needles. As valve, use can for example be made of the 750 V series of general purpose diaphragm valves of EFD. The bottom of these valves is provided with a tip adapter onto which tips 13, 14 of different sizes and showing in particular a different outlet 3, can be mounted. For controlling the operation of the dispense needles 11, 12, these needles are connected to a valve controller through the intermediary of pneumatic tubings 15, 16. Since the valve controller and the dispense needles are known per se, no further description will be given thereof.

In the apparatus illustrated in FIG. 4, the needles 11, 12 are mounted on a carriage 17 which is movable up and downwards, according to double arrow 18 (Z-direction) on a guiding support 19 by means of an electric motor 20. The multi-well plate which is to be filled with the liquid is to be inserted in a plate holder 21 situated underneath the needles 11, 12 and showing a recess 22 with dimensions adapted to the outer dimensions of the standard multi-well plates 2. The plate holder 21 is slideably mounted on a carriage 23 so that it can be moved, according to a reciprocating movement, in the direction of double arrow 24 (X-direction) on the carriage 23 by means of an electric motor 25 which is also mounted on this carriage 23. In order to be able to move the plate holder 21 in two dimensions, the carriage 23 is slideably mounted, in the direction of double arrow 26 (Y-direction), onto a guiding support 27. This guiding support 27 is mounted within the frame and is provided with an electric motor 28 for moving the carriage 23, and hence the plate holder 21, in the Y-direction.

The apparatus shown in FIG. 4 comprises a programmable control unit for controlling the operation of the valve controller and the operation of the motors 20, 25 and 28, i.e. the movements of the dispense needles 11, 12 in the Z-direction and the movements of the plate holder 21 in the X- and Y-direction. The control unit is further adapted to provide a dispensing and a non-dispensing mode. Further details of the control unit and the construction of the apparatus in general will not be given since a person skilled in the art will readily be able to construct such an apparatus and since many modifications can be applied to the illustrated apparatus without departing from the scope of the present invention. If necessary a cover (not shown) can be provided for securing the dispensing area.

Turning now back to the method according to the preferred embodiment of the invention wherein a series of wells 1 of a multi-well plate 2 is filled with fluid from a reservoir 6 or 7 by passing the fluid outlet 3 of the needles 13 or 14 in a continuous movement over this series of wells 1 while dispensing an uninterrupted flow of fluid out of the outlet, it will be clear that only a relative movement of the outlet 3 with respect of the multi-well plate 2 is required and that in other words either the outlet 3 and/or, as in the apparatus illustrated in FIG. 4, the plate 2 are moved.

For adding the fluid into the wells 1 of the plate 2 illustrated in FIG. 1, the different wells thereof could be considered as one series of wells which can be filled by one continuous movement of the outlet over the multi-well plate according to a pattern going from one well to the other and covering the entire surface of this plate. In this case, the movement direction of the outlet has however to be changed above certain wells so that very sudden changes of direction are required in order to avoid that the "corner" wells receive too much fluid (unless for example the wells on two opposite sides of the well may contain more fluid or unless the flow of fluid is interrupted when passing from one well to another).

Figure 2:
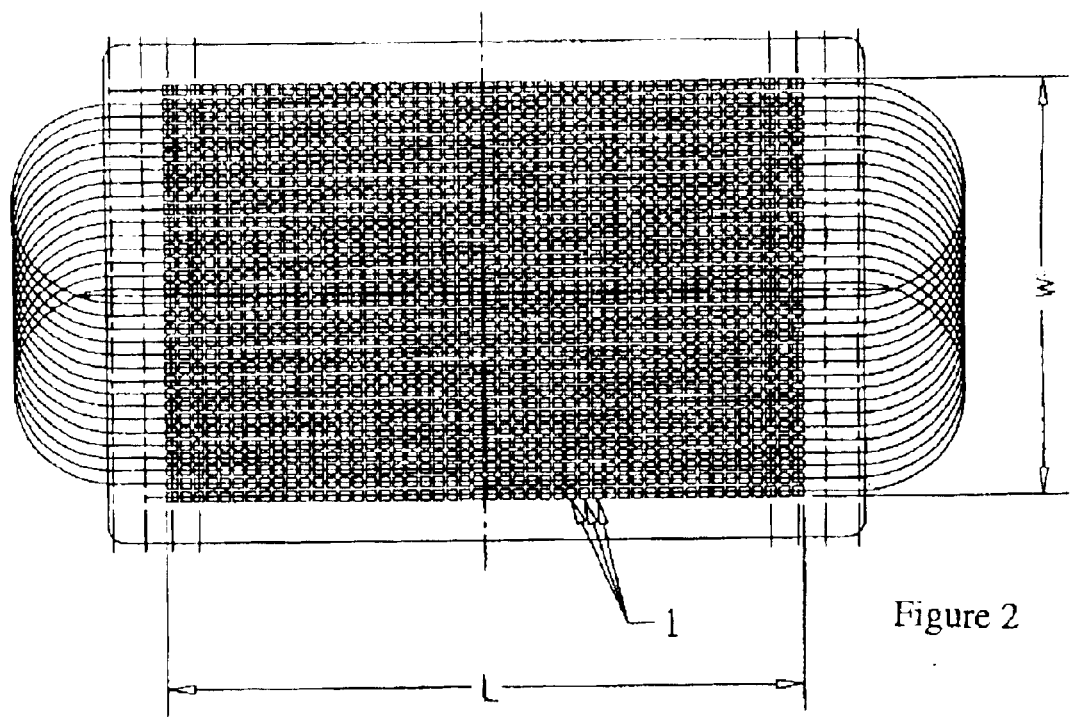
FIG. 2 shows a pattern that may be followed by the liquid outlet to fill the 1536 well plate of FIG. 1.

In a preferred embodiment of the invention, the array of wells 1 of the multi-well plate 2 is therefore divided in several substantially parallel series of wells, in particular rows or columns, extending from one side of the array to the other. In that case a pattern as illustrated in FIG. 2 can be followed. According to this pattern, when having passed over one row, the fluid outlet 3 turns in an area outside the array of wells 1 to another row of wells. In this way, the volume of fluid introduced in the wells at both opposite ends of the plate is easier to control. Moreover, a less sharp turning has to be made when returning not in the next row but as illustrated in FIG. 2, by skipping a number of rows and by filling these rows during the next turns.

Figure 5:
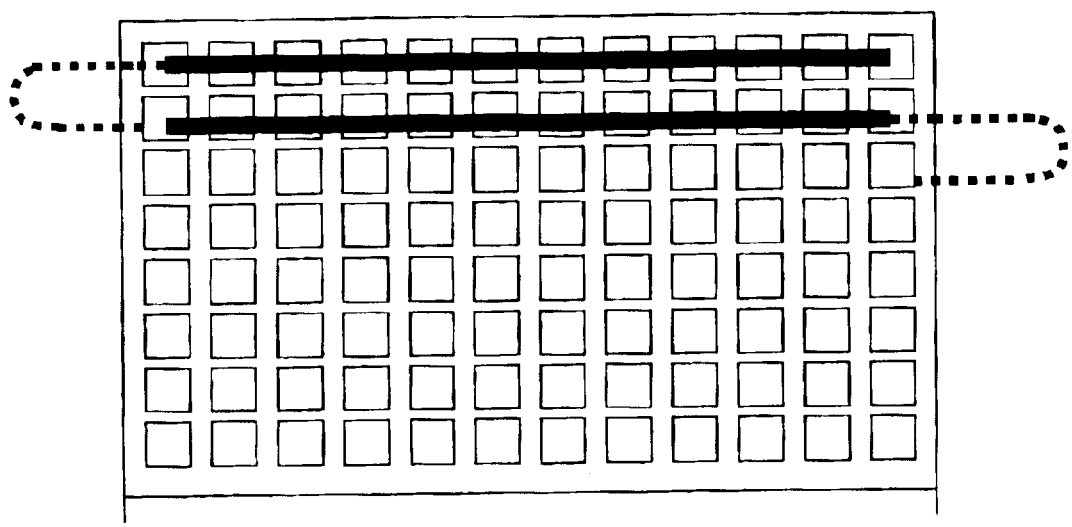
FIG. 5 shows schematically an embodiment of the method performed over a 96 well plate.

FIG. 5 provides for another embodiment of the method over a 96 well plate in which the dispensing mode is indicated in the bold straight lines and the interrupted curved lines indicate the non-dispensing mode. Preferably bend section of the curved motion is performed outside the area of the support, such that no risk for dispensing a loose droplet can occur. More preferably a straight lined motion as an extension of the turn or bend is provided in the non dispensing mode such that when again the mode is switched to the dispensing mode a constant speed is already available for the fluid outlet.

When passing over the area outside the array of wells, the flow of fluid out of the fluid outlet is preferably interrupted. Before passing over a next series of wells, the flow of fluid is started again, preferably somewhat in advance so as to fill the first well of each series at the required flow rate.

As described here-above, the apparatus illustrated in FIG. 4 comprises two dispense needles 11 and 12 with a fluid outlet 3 and two fluid reservoirs 6, 7. These reservoirs 6, 7 may be filled with the same or with different fluids. When filled with the same fluid, it is of course possible to connect both outlets 3 to one and the same reservoir.

Figure 3:
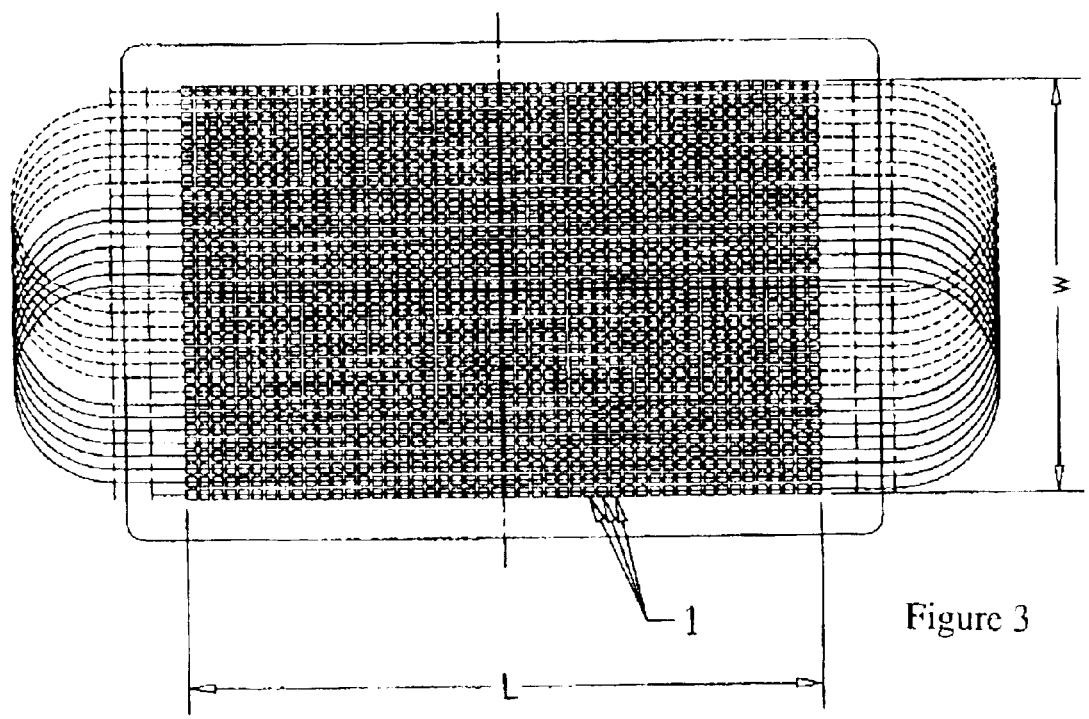
FIG. 3 shows an alternative pattern which may be followed to fill the 1536 well plate when use is made of two liquid outlets in a fixed position with respect to one another.

Both fluid outlets are fixed in the carriage 17 on a fixed distance from each other. This distance may correspond for example to half the number of rows of the multi-well plate. In this way, the plate can be filled according to a pattern as illustrated in FIG. 3, whereby each outlet follows, on one half of the plate, a pattern similar to the pattern illustrated in FIG. 2. It will be clear that with more outlets, similar patterns can be followed.

In a preferred embodiment, when the outlet 3 passes over one of said series of wells 1, the fluid is dispensed at a substantially constant flow rate out of the outlet. When the fluid outlet moves at a substantially constant speed with respect to the multi-well plate when it passes over this series of wells, a substantially constant volume of fluid is dispensed in the different wells of this series.

If desired, the speed of the outlet with respect to the multi-well plate can either continuously or discontinuously be increased or decreased when passing over a series of wells. In this way, the volume of fluid introduced in the wells will increase or decrease accordingly.

The flow rate at which the fluid is dispensed out of the outlet may for example be comprised between 0.001 and 2000 $\mu$l/sec and preferably between 10 and 1000 $\mu$l/sec and more preferably between 200 and 500 $\mu$l/sec. The volume of fluid which may be added into each well may vary within wide ranges, in particular between 0.00025 and 100 $\mu$l. In case the flow rate comprises for example 350 $\mu$l/sec, one row of a 1536 well plate (32×48 wells) would for example be filled with 7 $\mu$l per well in about 1 sec. Filling the entire plate would take then about half a minute. Filling a row of a plate with a larger number of wells may require substantially the same time since each of the wells has normally to be filled with less fluid. Filling a 3456 well plate (48×72 wells) would take then about 50 sec, or even less in case two or more dispense outlets are used.

The above flow rates enable the use of very narrow needle tips or outlet openings. The outlets may have for example an inner diameter of between 40 and 500 $\mu$m, and more particularly of between 50 and 200 $\mu$m, at least in case the fluid has a viscosity comparable to the viscosity of water. It will be clear that such narrow jets of fluid will enable to fill multi-well plates having even up to 9600 wells (80×120 wells) on the standard area of about 109×73 mm. In this way, even multi-well plates having such an extremely high number of wells could be filled with fluid in an acceptable period of time by employing the method according to the invention.

In the method according to a further aspect of the invention, the relatively narrow flow of fluid dispensed out of the outlet is partially deposited onto the top surfaces of the walls separating the wells. It has been found that this volume of fluid is however substantially equally divided over two successive wells when these wells are adjacent to one another. Preferably, the top surface of the partition walls between the wells is repellent for the fluid which is to be introduced therein so that small droplets are formed which roll off this surface so that no fluid remains on top thereof. Making this top surface somewhat convex, pointed or inclined can of course enhance this phenomenon. In the area where the fluid outlet or in other words the flow of fluid passes, the top surfaces of the partition walls between the wells have preferably a width smaller than 1 mm, and in particular smaller than 0.6 mm. Depending on the surface tension of the fluid and the adherence between the fluid and the surface of the partition walls, substantially no fluid will remain on top of such walls, even if these walls have no convex but a flat top surface. The constant speed of the fluid outlet relative to the series of wells in the dispensing mode is in general smaller than 300 mm/sec and preferably about 150 mm/sec.

From the above description, it will be clear that many modifications can be applied to the described embodiments without leaving the scope of the annexed claims.

It is for example possible to provide a fluid reservoir in the dispense needles 11, 12 themselves so that the tubings 9 and 10 can be omitted. Further, instead of moving the dispense needles 11, 12, it is also possible to move the plate holder 21 or to move the dispense needles 11, 12 in one direction and the plate holder 21 in another direction.

The plate holder 21 may also be arranged to carry two or more multi-well plates. In this case, the dispense needles are preferably arranged on such a mutual distance that they move each simultaneously above one of the multi-well plates.

Finally, instead of using valves in the dispense needles and a pressurized source of fluid, a pump could be provided in the tubings leading from the reservoirs 7, 8 to the dispense needles.

FIGS. 6, 7, 8 and 9 show four examples of filled 1536 well plates using the method of the invention. A rhodamine suspension is dispensed in these 1536 wells in a intermittent pattern of dispensing mode over the well in a straight line with a constant speed and a non-dispensing mode when moving from the filled series to a series to be filled. The plates were scanned and the pixel values calculated. The deviation was correlated to a deviation in volume and depicted into each well. As clearly visualized a very small deviation is obtained. In order to further improve the dispensing method a specific control program is designed. A main characteristic of said control is that the dispensing valve has a certain reaction time which becomes clear in the fact that the first and the last well of a series have a rather higher deviation. When taken the latter into account by providing a lead-in and a lead-out respectively at the beginning and at the end of the dispensing mode lower deviation is obtained.

What is claimed is:

1. Method for dispensing a predetermined volume of a fluid from a reservoir, through a fluid outlet in fluid communication with said reservoir, into each well of at least one series of wells, such that the volume in each of said well is substantially equal, whereby the method comprises a dispensing mode and a non-dispensing mode, whereby the dispensing mode is characterized in that, the fluid is dispensed at a continuous uninterrupted flow from a moving fluid outlet into said series of wells.

2. Method according to claim 1, wherein the dispensing mode is further characterized in a movement of the fluid outlet relatively to said series of wells at a constant relative speed with respect to the series of wells when passing over said series of wells.

3. Method according to claim 1, wherein the fluid outlet is moved along a straight line over the series of wells, whereby said series of wells consist essentially of wells arranged in a straight line.

4. Method according to claim 1, wherein the non-dispensing mode is characterized in that no fluid is being dispensed.

5. Method according to claim 4, wherein the non-dispensing mode is further characterized by the movement of the fluid outlet from a first series of wells to a second series of wells in curved and/or straight lines whereby said series of wells consists essentially of wells arranged in a straight line preferably parallel to each other.

6. Method according to claim 5, wherein the curved and/or straight lines form a bend from a first series of wells to a second series of wells.

7. Method according to claim 6, whereby the bend is a bend over 180°, preferably having a straight lined extension at the end of the bend.

8. Method according to claim 7, whereby the bend is a circular bend.

9. Method according to claim 1, characterized in that the fluid is dispensed at a flow rate of between 0.001 and 2000 $\mu$l/sec and preferably at a flow rate of between 10 and 1000:1/sec and more preferably between 200 and 500 $\mu$l/sec.

10. Method according to claim 1, characterized in that the continuous speed of said fluid outlet is smaller than 300 mm/sec and preferably around 150 mm/sec.

11. Method according to claim 1, characterized in that said predetermined dispensed volume per well in a series of wells is between 0.00025 and 100 $\mu$l.

12. Method according to claim 1, characterized in that said series of wells is included in a support of several series of wells, extending parallel from one side of the support to the other, whereby said series of wells are being filled in the dispensing mode with a predetermined volume of fluid by passing said outlet over said support.

13. Method according to claim 12, whereby after having added said predetermined volume of fluid into each well of one of a first series of wells, said fluid outlet is moved with respect to the support in a non-dispensing mode in an area outside said support to pass to a second series of wells.

14. Method according to claim 1, in which the average difference in volume of the dispensed fluid into each well is less than 10%, preferably about 5% or less, more preferably about 4% or less and most preferably about 3% or less.

15. Micro titer plate constructed from a hydrophobic and more in particular from a plastic material containing a plurality of parallel extending series of wells forming an array of wells, whereby the number of wells can for example be 96 organized as an array of twelve series of eight wells or any other number of wells such as 384, 864, 1536, 9600 containing a fluid dispensed in said wells by using the method according to claim 1.

16. Micro titer plate according to claim 15, wherein the average deviation in volume of the wells is less than 10%, preferably about 5% or less, more preferably about 4% or less and most preferably about 3% or less.

17. Apparatus for dispensing a volume of fluid from a reservoir, through a fluid outlet in fluid communication with said reservoir comprising:

a fluid outlet having an inlet and an outlet end for dispensing an uninterrupted flow of fluid originating from said reservoir onto a support comprising a series of wells, said support and/or a fluid outlet being secured in association with a table or carrier able to provide a relative X, X-Y or X-Y-Z motion between the support and the fluid outlet, and pumping means for providing an uninterrupted flow of fluid through the fluid outlet from the reservoir and a controller adapted to provide a dispensing and a non-dispensing mode, whereby the controller further is able to provide a substantial equal volume of fluid to be dispensed into each well during a dispensing mode.

18. Apparatus according to claim 17 whereby the fluid outlet comprises a valve adapted to be closed when a dispensing mode is being followed by a non-dispensing mode or to be opened when a non-dispensing mode is followed by a dispensing mode.

19. Apparatus according to claim 17, whereby the dimension of the apparatus is such that a cover is provided for securing the dispensing area.

* * * * *

UNITED STATES PATENT AND TRADEMARK OFFICE
CERTIFICATE OF CORRECTION

PATENT NO. : 6,868,875 B2  Page 1 of 1
APPLICATION NO. : 10/220931
DATED : March 22, 2005
INVENTOR(S) : Werner René Irène De Beukeleer et al.

It is certified that error appears in the above-identified patent and that said Letters Patent is hereby corrected as shown below:

Column 9, Claim 9, Line 35, delete ":" and insert --µ--.

Signed and Sealed this

Twentieth Day of March, 2007

JON W. DUDAS
*Director of the United States Patent and Trademark Office*